(12) United States Patent
Ryan et al.

(10) Patent No.: US 8,262,659 B2
(45) Date of Patent: Sep. 11, 2012

(54) TRANSLATABLE CARRIAGE FIXATION SYSTEM

(75) Inventors: Christopher J. Ryan, West Chester, PA (US); Sean S. Suh, Plymouth Meeting, PA (US); David S. Rathbun, Gap, PA (US); Christoph A Roth, West Chester, PA (US); David Koch, Coatesville, PA (US)

(73) Assignee: Synthes USA, LLC, West Chester, PA (US)

( * ) Notice: Subject to any disclaimer, the term of this patent is extended or adjusted under 35 U.S.C. 154(b) by 0 days.

(21) Appl. No.: 12/690,806

(22) Filed: Jan. 20, 2010

(65) Prior Publication Data

US 2010/0121329 A1     May 13, 2010

Related U.S. Application Data

(60) Division of application No. 11/217,959, filed on Aug. 31, 2005, now Pat. No. 7,666,185, which is a continuation-in-part of application No. 10/932,392, filed on Sep. 2, 2004, now abandoned, which is a continuation-in-part of application No. 10/653,164, filed on Sep. 3, 2003, now Pat. No. 7,857,839.

(51) Int. Cl.
*A61B 17/56* (2006.01)

(52) U.S. Cl. .......................................... 606/71

(58) Field of Classification Search ............ 606/71, 606/280–299
See application file for complete search history.

(56) References Cited

U.S. PATENT DOCUMENTS

| 408,080 A | 7/1889 | Carroll |
| 1,025,008 A | 4/1912 | Miner |
| 2,406,832 A | 9/1946 | Hardinge |
| 2,486,303 A | 10/1949 | Longfellow |
| 3,068,869 A | 12/1962 | Shelden et al. |
| 3,244,170 A | 4/1966 | McElvenny |
| 3,547,114 A | 12/1970 | Haboush |

(Continued)

FOREIGN PATENT DOCUMENTS

CN     00136708.0     7/2002

(Continued)

OTHER PUBLICATIONS

AESCULAP ABC, Anterior Cervical Plating System, Advanced Biomechanical Concept.

(Continued)

*Primary Examiner* — Eduardo C Robert
*Assistant Examiner* — Summer Kostelnik
(74) *Attorney, Agent, or Firm* — Woodcock Washburn LLP

(57) ABSTRACT

Translational bone fixation assemblies, kits containing such assemblies, and methods of use are described herein. The described assemblies may be used in spinal fusion procedures in which a damaged or diseased disc (or part of a disc) is removed from between a pair of vertebrae and a spinal fusion spacer is placed between the vertebrae. The assemblies may be applied to an anterior portion of the affected vertebrae to span the affected disc space, and may be fixed to the vertebrae using bone screws. The assemblies may function to maintain the vertebrae aligned during the initial period following fixation in which fusion of the spacer to the adjacent vertebrae occurs. The assemblies may also function to share some of the axial spinal load applied to the fusion spacer to prevent extreme subsidence of the spacer into the vertebral body, such as where the patient has poor bone quality.

20 Claims, 31 Drawing Sheets

U.S. PATENT DOCUMENTS

| | | |
|---|---|---|
| 3,604,414 A | 9/1971 | Borges |
| 3,659,595 A | 5/1972 | Haboush |
| 4,270,248 A | 6/1981 | Akashi |
| RE31,628 E | 7/1984 | Allgower et al. |
| 4,493,317 A | 1/1985 | Klaue |
| 4,513,744 A | 4/1985 | Klaue |
| 4,611,581 A | 9/1986 | Steffee |
| 4,696,290 A | 9/1987 | Steffee |
| 4,790,297 A | 12/1988 | Luque |
| 4,836,196 A | 6/1989 | Park et al. |
| 4,913,134 A | 4/1990 | Luque |
| 4,957,497 A | 9/1990 | Hoogland et al. |
| 5,002,542 A | 3/1991 | Frigg |
| 5,129,899 A | 7/1992 | Small et al. |
| 5,180,382 A | 1/1993 | Frigg |
| 5,209,751 A | 5/1993 | Farris et al. |
| 5,234,431 A | 8/1993 | Keller |
| 5,269,784 A | 12/1993 | Mast |
| 5,290,288 A | 3/1994 | Vignaud et al. |
| 5,324,290 A | 6/1994 | Zdeblick et al. |
| 5,344,422 A | 9/1994 | Frigg |
| 5,364,399 A | 11/1994 | Lowery et al. |
| 5,387,212 A | 2/1995 | Yuan et al. |
| 5,403,136 A | 4/1995 | Mathys |
| 5,423,826 A | 6/1995 | Coates et al. |
| 5,437,669 A | 8/1995 | Yuan et al. |
| 5,470,333 A | 11/1995 | Ray |
| 5,480,440 A | 1/1996 | Kambin |
| 5,484,439 A | 1/1996 | Olson et al. |
| 5,486,176 A | 1/1996 | Hildebrand et al. |
| 5,498,263 A | 3/1996 | DiNello et al. |
| 5,501,684 A | 3/1996 | Schlapfer |
| 5,527,315 A | 6/1996 | Jeanson et al. |
| 5,531,745 A | 7/1996 | Ray |
| 5,531,747 A | 7/1996 | Ray |
| 5,540,690 A | 7/1996 | Miller et al. |
| 5,545,163 A | 8/1996 | Miller et al. |
| 5,545,228 A | 8/1996 | Kambin |
| 5,549,612 A | 8/1996 | Yapp |
| 5,578,034 A | 11/1996 | Estes |
| 5,584,887 A | 12/1996 | Kambin |
| 5,601,553 A | 2/1997 | Trebing |
| 5,616,142 A | 4/1997 | Yuan et al. ............... 606/61 |
| 5,616,144 A | 4/1997 | Yapp et al. |
| 5,620,443 A | 4/1997 | Gertzbein et al. |
| 5,643,265 A | 7/1997 | Errico |
| 5,672,177 A | 9/1997 | Seldin |
| 5,676,666 A | 10/1997 | Oxland et al. |
| 5,676,667 A | 10/1997 | Hausman |
| 5,681,312 A | 10/1997 | Yuan |
| 5,702,395 A | 12/1997 | Hopf |
| 5,707,372 A | 1/1998 | Errico et al. |
| 5,709,686 A | 1/1998 | Talos |
| 5,713,900 A | 2/1998 | Benzel et al. |
| 5,733,287 A | 3/1998 | Tepic |
| 5,741,258 A | 4/1998 | Klaue |
| 5,800,433 A | 9/1998 | Benzel et al. |
| 5,800,435 A | 9/1998 | Errico et al. |
| 5,810,823 A | 9/1998 | Klaue |
| 5,827,286 A | 10/1998 | Incavo et al. |
| 5,843,082 A | 12/1998 | Yuan et al. |
| 5,851,207 A | 12/1998 | Cesarone |
| 5,855,580 A | 1/1999 | Kreidler et al. |
| 5,876,402 A | 3/1999 | Errico et al. |
| 5,899,906 A | 5/1999 | Schenk |
| 5,902,303 A | 5/1999 | Eckhof et al. |
| 5,902,304 A | 5/1999 | Walker et al. |
| 5,904,683 A | 5/1999 | Pohndorf et al. |
| 5,931,838 A | 8/1999 | Vito |
| 5,954,722 A | 9/1999 | Bono |
| 5,964,761 A | 10/1999 | Kambin |
| 5,964,762 A | 10/1999 | Biedermann et al. |
| 5,964,763 A | 10/1999 | Incavo et al. ............... 606/71 |
| 5,976,141 A | 11/1999 | Haag |
| 5,997,541 A | 12/1999 | Schenk |
| 6,004,322 A | 12/1999 | Bernstein |
| 6,004,323 A | 12/1999 | Park et al. |
| 6,017,345 A | 1/2000 | Richelsoph |
| 6,030,389 A | 2/2000 | Wagner et al. |
| 6,048,344 A | 4/2000 | Schenk |
| 6,063,090 A | 5/2000 | Schlapfer |
| 6,066,140 A | 5/2000 | Gertzbein et al. |
| 6,083,224 A | 7/2000 | Gertzbein et al. |
| 6,106,526 A | 8/2000 | Harms et al. |
| 6,117,135 A | 9/2000 | Schlapfer |
| 6,117,173 A | 9/2000 | Taddia et al. |
| 6,136,002 A | 10/2000 | Shih et al. |
| 6,139,550 A | 10/2000 | Michelson |
| 6,152,927 A | 11/2000 | Farris et al. |
| 6,156,037 A | 12/2000 | LeHuec et al. |
| 6,176,861 B1 | 1/2001 | Bernstein et al. |
| 6,187,005 B1 | 2/2001 | Brace |
| 6,193,720 B1 | 2/2001 | Yuan et al. |
| 6,193,721 B1 | 2/2001 | Michelson |
| 6,206,881 B1 | 3/2001 | Frigg |
| 6,224,602 B1 | 5/2001 | Hayes |
| 6,235,033 B1 | 5/2001 | Brace |
| 6,235,034 B1 | 5/2001 | Bray, Jr. |
| 6,254,603 B1 | 7/2001 | Gertzbein et al. |
| 6,258,089 B1 | 7/2001 | Campbell et al. |
| 6,261,291 B1 | 7/2001 | Talaber et al. |
| 6,273,889 B1 | 8/2001 | Richelsoph |
| 6,277,124 B1 | 8/2001 | Haag |
| 6,280,445 B1 | 8/2001 | Morrison et al. |
| 6,287,309 B1 | 9/2001 | Baccelli et al. |
| 6,293,949 B1 | 9/2001 | Justis et al. |
| 6,302,883 B1 | 10/2001 | Bono |
| 6,306,136 B1 | 10/2001 | Baccelli |
| 6,306,140 B1 | 10/2001 | Siddiqui |
| 6,309,393 B1 | 10/2001 | Tepic |
| 6,315,779 B1 | 11/2001 | Morrison et al. |
| 6,328,738 B1 | 12/2001 | Suddaby |
| 6,331,179 B1 | 12/2001 | Fried et al. |
| 6,342,055 B1 | 1/2002 | Eisermann et al. |
| 6,342,057 B1 | 1/2002 | Brace et al. |
| 6,355,038 B1 | 3/2002 | Pisharodi |
| 6,361,537 B1 | 3/2002 | Anderson |
| 6,379,357 B1 | 4/2002 | Bernstein et al. |
| 6,383,186 B1 | 5/2002 | Michelson |
| 6,398,783 B1 | 6/2002 | Michelson |
| 6,402,756 B1 | 6/2002 | Ralph et al. |
| 6,416,528 B1 | 7/2002 | Michelson |
| 6,423,069 B1 | 7/2002 | Sellers |
| 6,428,542 B1 | 8/2002 | Michelson |
| 6,432,108 B1 | 8/2002 | Burgess et al. |
| 6,454,769 B2 | 9/2002 | Wagner et al. |
| 6,454,771 B1 | 9/2002 | Michelson |
| 6,471,704 B2 | 10/2002 | Gertzbein et al. |
| 6,471,706 B1 | 10/2002 | Schumacher et al. |
| 6,503,250 B2 | 1/2003 | Paul |
| 6,527,776 B1 | 3/2003 | Michelson |
| 6,533,786 B1 | 3/2003 | Needham et al. |
| 6,575,975 B2 | 6/2003 | Brace et al. |
| 6,585,738 B1 | 7/2003 | Mangione et al. |
| 6,592,586 B1 | 7/2003 | Michelson |
| 6,599,290 B2 | 7/2003 | Bailey et al. |
| 6,602,254 B2 | 8/2003 | Gertzbein et al. |
| 6,602,255 B1 | 8/2003 | Campbell et al. |
| 6,602,256 B1 | 8/2003 | Hayes |
| 6,610,062 B2 | 8/2003 | Noblitt et al. |
| 6,616,666 B1 | 9/2003 | Michelson |
| 6,620,163 B1 | 9/2003 | Michelson |
| 6,641,583 B2 | 11/2003 | Shluzas et al. |
| 6,645,207 B2 | 11/2003 | Dixon et al. |
| 6,645,208 B2 | 11/2003 | Apfelbaum et al. |
| 6,663,632 B1 | 12/2003 | Frigg |
| 6,666,867 B2 | 12/2003 | Ralph et al. |
| 6,669,697 B1 | 12/2003 | Pisharodi |
| 6,682,530 B2 | 1/2004 | Dixon et al. |
| 6,689,133 B2 | 2/2004 | Morrison et al. |
| 6,689,134 B2 | 2/2004 | Ralph et al. |
| 6,692,503 B2 | 2/2004 | Foley et al. |
| 6,695,846 B2 | 2/2004 | Richelsoph et al. |
| 6,699,249 B2 | 3/2004 | Schlapfer et al. |
| 6,702,817 B2 | 3/2004 | Beger et al. |
| 6,712,818 B1 | 3/2004 | Michelson |
| RE38,684 E | 1/2005 | Cesarone |

| | | |
|---|---|---|
| 6,872,210 B2 | 3/2005 | Hearn |
| 7,008,427 B2 | 3/2006 | Sevrain |
| 7,186,254 B2 | 3/2007 | Dinh et al. |
| 7,220,263 B2 | 5/2007 | Cordaro |
| 7,357,804 B2 | 4/2008 | Binder, Jr. et al. |
| 2001/0010000 A1 | 7/2001 | Gertzbein et al. |
| 2001/0014807 A1 | 8/2001 | Wagner et al. |
| 2001/0037111 A1 | 11/2001 | Dixon et al. |
| 2001/0037112 A1 | 11/2001 | Brace et al. |
| 2001/0041894 A1 | 11/2001 | Campbell et al. |
| 2002/0013586 A1 | 1/2002 | Justis et al. |
| 2002/0026194 A1 | 2/2002 | Morrison et al. |
| 2002/0029040 A1 | 3/2002 | Morrison et al. |
| 2002/0045896 A1 | 4/2002 | Michelson |
| 2002/0045897 A1 | 4/2002 | Dixon et al. |
| 2002/0045898 A1 | 4/2002 | Freid et al. |
| 2002/0045899 A1 | 4/2002 | Errico et al. |
| 2002/0055741 A1 | 5/2002 | Schlapfer et al. |
| 2002/0058939 A1 | 5/2002 | Wagner et al. |
| 2002/0065517 A1 | 5/2002 | Paul |
| 2002/0077630 A1 | 6/2002 | Lin |
| 2002/0111630 A1 | 8/2002 | Ralph et al. |
| 2002/0116002 A1 | 8/2002 | Sellers |
| 2002/0120273 A1 | 8/2002 | Needham et al. |
| 2002/0128655 A1 | 9/2002 | Michelson |
| 2002/0143328 A1 | 10/2002 | Shluzas et al. |
| 2002/0143336 A1 | 10/2002 | Hearn |
| 2002/0151896 A1 | 10/2002 | Ferree |
| 2002/0151899 A1 | 10/2002 | Bailey et al. |
| 2002/0161367 A1 | 10/2002 | Ferree |
| 2002/0183749 A1 | 12/2002 | Burgess et al. |
| 2002/0183754 A1 | 12/2002 | Michelson |
| 2002/0183755 A1 | 12/2002 | Michelson |
| 2002/0183756 A1 | 12/2002 | Michelson |
| 2002/0183757 A1 | 12/2002 | Michelson |
| 2002/0188296 A1 | 12/2002 | Michelson |
| 2002/0193795 A1 | 12/2002 | Gertzbein et al. |
| 2003/0018335 A1 | 1/2003 | Michelson |
| 2003/0028250 A1 | 2/2003 | Reiley et al. |
| 2003/0036759 A1 | 2/2003 | Musso |
| 2003/0040749 A1 | 2/2003 | Grabowski et al. |
| 2003/0045875 A1 | 3/2003 | Bertranou et al. |
| 2003/0045880 A1 | 3/2003 | Michelson |
| 2003/0050640 A1 | 3/2003 | Lee et al. |
| 2003/0060828 A1* | 3/2003 | Michelson ............ 606/71 |
| 2003/0074001 A1 | 4/2003 | Apfelbaum et al. |
| 2003/0093082 A1 | 5/2003 | Campbell et al. |
| 2003/0105462 A1 | 6/2003 | Haider et al. |
| 2003/0105463 A1 | 6/2003 | Wolgen |
| 2003/0114856 A1 | 6/2003 | Nathanson et al. |
| 2003/0130661 A1 | 7/2003 | Osman ............ 606/71 |
| 2003/0135210 A1 | 7/2003 | Dixon et al. |
| 2003/0149434 A1 | 8/2003 | Paul |
| 2003/0153920 A1 | 8/2003 | Ralph et al. |
| 2003/0171752 A1 | 9/2003 | Assaker et al. |
| 2003/0187440 A1 | 10/2003 | Richelsoph et al. |
| 2003/0187442 A1 | 10/2003 | Richelsoph et al. |
| 2003/0187443 A1 | 10/2003 | Lauryssen et al. |
| 2003/0204190 A1 | 10/2003 | Li |
| 2003/0208203 A1 | 11/2003 | Lim et al. |
| 2003/0212399 A1 | 11/2003 | Dinh et al. ............ 606/61 |
| 2003/0225409 A1 | 12/2003 | Freid et al. |
| 2003/0229348 A1 | 12/2003 | Sevrain |
| 2004/0006343 A1 | 1/2004 | Sevrain |
| 2004/0019353 A1 | 1/2004 | Freid et al. ............ 606/69 |
| 2004/0030338 A1 | 2/2004 | Paul |
| 2004/0039388 A1 | 2/2004 | Biedermann et al. |
| 2004/0068319 A1 | 4/2004 | Cordaro |
| 2004/0087951 A1 | 5/2004 | Khalili |
| 2004/0097935 A1 | 5/2004 | Richelsoph et al. |
| 2004/0127899 A1 | 7/2004 | Konieczynski et al. |
| 2004/0167521 A1 | 8/2004 | De Windt |
| 2004/0204712 A1 | 10/2004 | Kolb et al. ............ 606/69 |
| 2004/0260306 A1 | 12/2004 | Fallin et al. |
| 2005/0015092 A1 | 1/2005 | Rathbun et al. |
| 2005/0049593 A1 | 3/2005 | Duong et al. |
| 2005/0192577 A1 | 9/2005 | Mosca et al. |

FOREIGN PATENT DOCUMENTS

| | | |
|---|---|---|
| DE | 4007306 C1 | 5/1991 |
| DE | 10015734 A1 | 9/2001 |
| EP | 599640 A1 | 6/1994 |
| EP | 0 684 017 A1 | 11/1995 |
| EP | 689799 A1 | 1/1996 |
| EP | 726064 A2 | 8/1996 |
| EP | 739610 A2 | 10/1996 |
| EP | 739610 A3 | 2/1997 |
| EP | 773004 A1 | 5/1997 |
| EP | 829240 A1 | 3/1998 |
| EP | 599640 B1 | 8/1998 |
| EP | 726064 A3 | 10/1998 |
| EP | 829240 B1 | 3/1999 |
| EP | 904740 A2 | 3/1999 |
| EP | 904740 A3 | 5/1999 |
| EP | 689799 B1 | 9/2001 |
| EP | 1169971 A2 | 1/2002 |
| EP | 1 205 154 A2 | 5/2002 |
| EP | 1205154 A2 | 5/2002 |
| EP | 1 169971 A3 | 7/2002 |
| EP | 1 169 971 A2 | 9/2002 |
| EP | 1250892 A2 | 10/2002 |
| EP | 1285632 A1 | 2/2003 |
| EP | 1205154 A3 | 4/2003 |
| EP | 726064 B1 | 8/2003 |
| EP | 1250892 A3 | 9/2003 |
| EP | 1346697 A2 | 9/2003 |
| EP | 1348390 A2 | 10/2003 |
| EP | 739610 B1 | 12/2003 |
| EP | 1346697 A3 | 8/2004 |
| EP | 1169971 B1 | 10/2004 |
| FR | JP 2180249 A | 7/1990 |
| FR | JP 5111495 A | 5/1993 |
| FR | 2720623 A1 | 12/1995 |
| FR | 2763828 A1 | 12/1998 |
| FR | 2796829 A1 | 2/2001 |
| FR | 2810532 A1 | 12/2001 |
| FR | JP 2003310633 A | 11/2003 |
| WO | WO 91/07139 | 5/1991 |
| WO | WO 95/22937 A1 | 8/1995 |
| WO | WO 95/25474 A1 | 9/1995 |
| WO | WO 96/14802 A1 | 5/1996 |
| WO | WO 97/20512 A1 | 1/1997 |
| WO | WO 98/11837 A1 | 3/1998 |
| WO | WO 98/34553 A1 | 8/1998 |
| WO | WO 99/04718 A1 | 2/1999 |
| WO | WO 99/15094 A1 | 4/1999 |
| WO | WO 00/01314 A1 | 1/2000 |
| WO | WO 00/54681 A2 | 9/2000 |
| WO | WO 00/78238 A1 | 12/2000 |
| WO | WO 03/063714 A2 | 8/2003 |
| WO | WO 2004/093702 | 11/2004 |

OTHER PUBLICATIONS

AESCULAP,ABC, Anterior Cervical Plating System, Advanced Biomechanical Concept.
AESCULAP ABC, Anterior Cervical Plating System, Surgical Technique, Ronald I. Apfelbaum, M.D., contributions from José Bárbera, M.D., and Wolfhard Caspar, M.D., © 1999.
Blackstone Medical Inc., Blackstone™ Anterior Cervical Plate, The next-generation for easier implantation and reliable performance.
CODMAN, Anterior Cervical Plate System, Technique Guide.
Depuy Motech™ Restoring the Natural Balance, Introducing the Profile™ Anterior Thoracolumbar Compression Plate, © 1998.
Depuy Motech™ Restoring the Natural Balance, Introducing Peak™ Polyaxial Anterior Cervical Plate, © 1998.
DePuy Motech AcroMed™, Ventral Cervical Stabilization System.
DePuy AcroMed™, a Johnson & Johnson company, DOC™ Ventral Cervical Stabilization System, Surgical Technique, Edward C. Benzel, M.D., Facs, Hensen Yuan, M.D., Aug. 1999.
AcroMed, DOC Ventral Cervical Stabilization System, Surgical Technique, Edward C. Benzel, M.D>, FACS, Hansen Yuan, M.D., Feb. 1998.
Eurosurgical Ortho Tech REO SpineLine SpineNet, The Apex of Technology, Dec. 26, 2001.

Interpore Cross International, TPS Surgical Technique Summary, © 2000.
Interpore Cross International, C-TEK™ Anterior Cervical Plate, Surgical Technique, © 2001.
Interpore Cross International, Telescopic Plate SpacerTPS™ Spinal System, Surgical Technique for the Cervical Spine.
Medtronic SOFAMOR DANEK, Premier Anterior Cervical Plate System Surgical Technique, Thomas A. Zdeblick, MD, Harry N. Herkowitz, M.D.
Medtronic SOFAMOR DANEK, PLATE™ Anterior Fixation System, Surgical Technique, Thomas A. Zdeblick, M.D, © 1999.
Medtronic SOFAMOR DANEK, ZEPHIR™ Anterior Cervical System, Smoothly Natural, © Mar. 2000.
Medtronic SOFAMOR DANEK, ZEPHIR™ Anterior Cervical System, Smoothly Natural.
Medtronic SOFAMOR DANEK, ZEPHIR™ Anterior Cervical System, Surgical Technique, Richard Assaker, M.D., © Mar. 2000.
Medtronic SOFAMOR DANEK, Premier Anterior Cervical Plate System, © 2000.
Medtronic, SOFAMOR DANEK, ATLANTIS™ anterior cervical plate system, Surgical Technique, Volker K.H. Sonntag, M.D., Regis W. Haid, Jr., M.D., Stephen M. Papadopoulos, M.D.,.
SOFAMOR DANEK The Spine Specialist™, ATLANTIS™ anterior cervical plate system, © 1998.
SCIENT'X , PCB Cervical System.
SCIENT'X Secuplate, Surgical Technique.
Stryker, REFLEX™ Anterior Cervical Plate, REliable and FLEXible, May 2001.
Sulzer MEDICA, Sulzer Spine Tech, Trinica™ Anterior Cervical Plate System, Featuring Secure-Twis™ Anti-migration System, Aug. 2001.
Sulzer Medica, Sulzer Spine-Tech, Trinica™ Anterior Cervical Plate System Surgical Technique, Featuring Secure-Twist™ Anti-migration System,. Sep. 2001.
Synthes Spine, The Cervical Spine Locking Plate CSLP, Original Instruments and Implants of the Association for the Study of Internal Fixation—AO ASIF.
Ulrich medizintechnik, anterior distractable cage.
Ulrich medizintechnik, winged anterior distraction device ADD plus.
Wind W Cervical Stabilization System, Quick Reference Guide.
Chinese official action, dated Aug. 6, 2007, in Chinese Application No. 200480025309 with English translation.
Boothroyd et al., Product Design for Manufacture and Assembly, 1994, Marcel Dekker, Inc., pp. 64-67.
Moftakhar, M.D., Roham and Trost, M.D., Gregory R., "Anterior cervical plates: a historical perspective", Department of Neurosurgery, University of Wisconsin School of Medicine, Madison, Wisconsin, Neurosurg Focus, vol. 16 (1): Article 8, Jan. 2004.

* cited by examiner

A-A

B-B

F-F

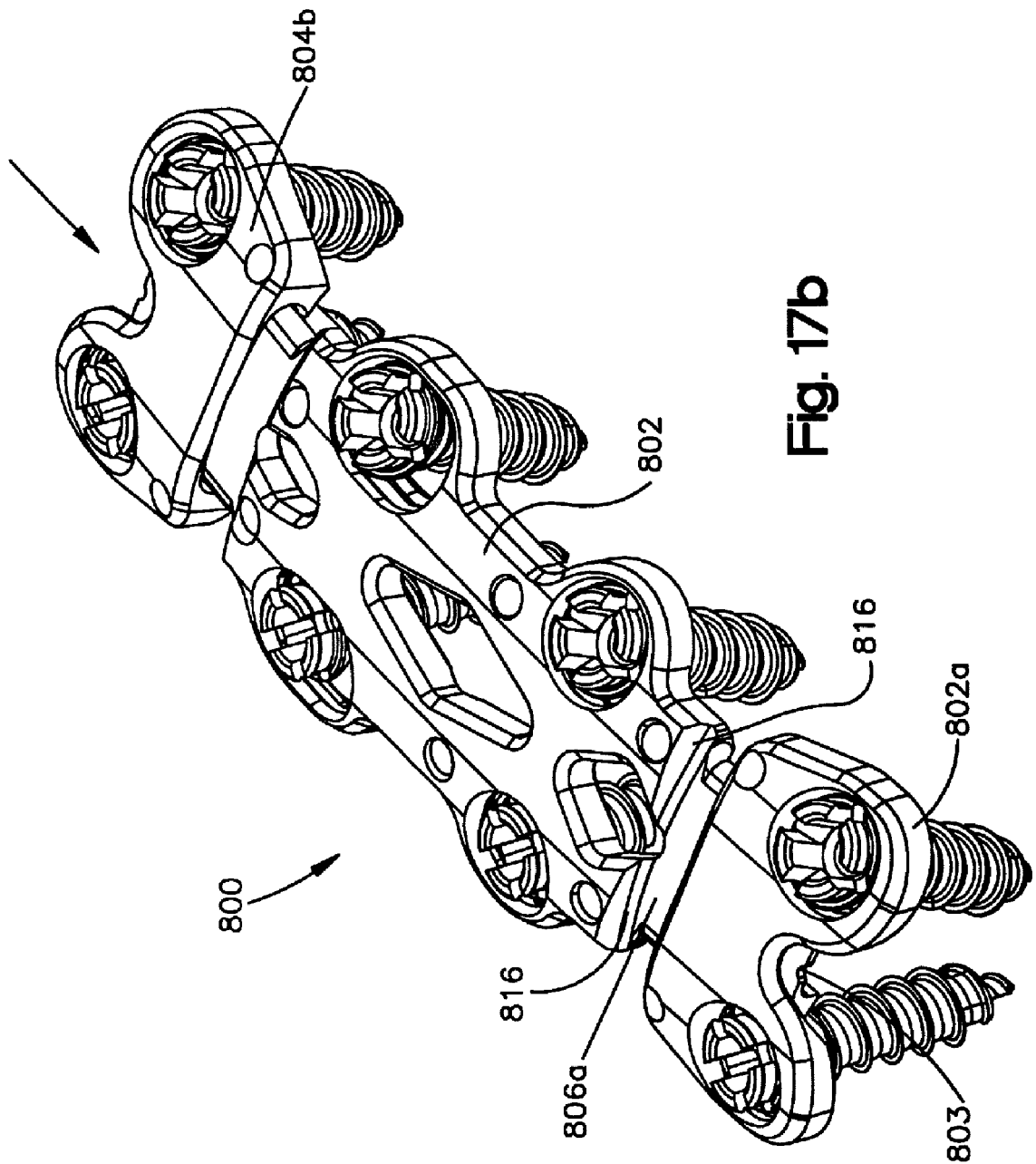

TRANSLATABLE CARRIAGE FIXATION SYSTEM

CROSS-REFERENCE TO RELATED APPLICATION

This application is a divisional application of U.S. application Ser. No. 11/217,959, filed Aug. 31, 2005 now U.S. Pat. No. 7,666,185, which is a continuation-in-part of U.S. patent application Ser. No. 10/932,392, filed Sep. 2, 2004 now abandoned, which is a continuation-in-part of U.S. patent application Ser. No. 10/653,164, filed Sep. 3, 2003 now U.S. Pat. No. 7,857,839, the entire disclosure of each application is expressly incorporated by reference herein.

FIELD OF THE INVENTION

The present invention is related to a fixation system. More particularly, the invention is related to a fixation system consisting of a translational plate system with a plurality of fixation holes.

BACKGROUND OF THE INVENTION

Orthopedic fixation devices such as plates are frequently coupled to bone with fasteners inserted through plate holes. It is known that securing such fasteners to the bone plate, for example through the use of expansion-head screws, can decrease the incidence of loosening of the fixation assembly post-operatively. It is also known that a bushing may be disposed in each plate hole to receive the fastener to permit polyaxial movement so that the fastener may be angulated at a surgeon-selected angle. However, polyaxial movement of fasteners through set plate hole locations only increases attachment alternatives of the fasteners themselves. The plate holes remain fixed in relation to each other and to the longitudinal axis of the plate.

Typically, a spinal fixation plate is applied to the anterior side of the affected vertebrae to span at least one affected disc space or vertebra (i.e. one in which at least a portion of the disc has been removed and a spinal fusion spacer has been inserted). The plate is fixed to the vertebrae using bone screws and acts to keep the vertebrae generally aligned during the initial period following fixation in which fusion of the spacer to the adjacent vertebrae occurs. The plate also may act to prevent the spacer from being expelled from the disc space during this initial period.

Where a spinal fusion spacer is implanted between a pair of vertebrae to be fused, the spacer rests on the endplates of the vertebrae. The outer circumference of the end plates comprises hard cortical bone and thus provides the best surface upon which to seat the spacer. The center portion of the endplates comprises a thin cortical bone shell overlying a core of softer cancellous bone. Most, if not all, of the spacer contact surface, however, may be located in this center portion.

Subsequent to placement of the spacer, the surgeon typically compresses the disc space by pressing the adjacent vertebrae together. This compression ensures a good engagement between the spacer and the endplates, increasing the chances that fusion will occur. Often in the period immediately following surgery, the spacer may subside slightly into the under-portion of the endplates, or the space between the vertebral endplates may decrease due to graft resorption (in the case of allograft spacers).

Where a rigid fixation plate is used to connect the vertebrae, this subsidence may tend to shift more of the spinal load to the plate than is desirable. Such load shifting can also occur due to inaccuracies in installing the plate to the vertebrae. In extreme circumstances, this load shifting can result in non-fusion of the spacer to the vertebra, since firm compression between the spacer and the vertebrae is one factor contributing to successful fusion.

Accordingly, there exists a need for a fixation system which provides the desired support to the vertebrae to be fused, and which allows limited translation of the vertebrae with respect to at least a portion of the plate, thereby limiting the undesirable effects of load shielding by the plate due to graft subsidence caused by settling or normal forces experienced in the spinal column. Promoting fusion of the adjacent vertebrae may thus accomplished.

Translation plates which compensate for this subsidence by providing the aforementioned benefits of a rigid fixation plate (general vertebral alignment, and prevention of spacer expulsion), while allowing at least one vertebra to move with respect to the plate to compensate for post-surgical subsidence, may be desirable. This compensation may permit the majority of the spinal column load to be borne by the spacer rather than the plate.

SUMMARY OF THE INVENTION

An embodiment of a bone fixation assembly is described, comprising: a first plate having a first end, a second end, a longitudinal axis, and upper surface, and a lower surface, the first plate having at least two fixation holes extending from the upper surface to the lower surface, the first plate further comprising first and second extending segments extending near the first end of the first plate in the direction of the longitudinal axis, the first extending segment associated with the upper surface and the second extending segment associated with the lower surface, and a first cavity formed between the extending segments; and at least one carriage block having at least two fixation holes; wherein the at least one carriage block is received and retained within the first cavity and is slidably moveable with respect to the first plate.

The first plate may further comprise a second cavity. The assembly may further comprise a second carriage block slidably associated with the first plate within the second cavity. The second carriage block may be slidable independent of the first carriage block. The second carriage block may comprise at least two fixation holes.

The first and second carriage blocks may be permitted to slide simultaneously. The first carriage block may be permitted to slide over a greater distance than that of the second carriage block. The sliding distance of the second carriage block may be limited by a motion-limiting element. The first carriage block may be permitted to slide from about 0 mm to about 10 mm relative to the first plate.

The first plate may further comprise at least one recess. The assembly may further comprise a securing element insertable in a recess. The securing element may be able to limit the translatable movement of the first carriage block along the longitudinal axis. At least one recess may extend from the upper surface to the lower surface. At least one recess may be substantially circular, substantially oblong, and/or substantially polygonal. At least one recess may be able to receive a drill guide, and/or a temporary attachment element.

The first plate may have four fixation holes, and wherein the fixation holes are arranged in pairs. The first plate further may comprise at least one indent able to facilitate the bending of the first plate. At least two fixation holes may be substantially circular, and may further comprise a clip. At least two fixation holes may be substantially oblong. At least two fixation holes may each have a longitudinal axis, and wherein the at least two fixation holes allow for the translation of a fastener along the longitudinal axis of each of the at least two fixation holes. At least two fixation holes may allow for selective placement of a fastener within each of the at least two fixation holes.

The first plate further may comprise at least one internal fixation element slidably associated with the first plate. At least one internal fixation element may further comprises at least one fixation hole. At least one internal fixation element may be slidably translatable in relation to the fixation holes of the first plate. At least one internal fixation element may also be slidably translatable in relation to the fixation holes of the first carriage block. The first plate may further comprise a groove, and wherein at least one internal fixation element is able to situated in the groove.

The first carriage block may experience a frictional force of at least 50 grams when slidably moving in relation to the first plate.

The first and second extending segments may each have a longitudinal axis, and wherein the longitudinal axes of the first and second extending segments are divergent. The first and second extending segments may also each have a longitudinal axis, and wherein the longitudinal axes of the first and second extending segments are convergent. Further, the first and second extending segments may each have a longitudinal axis, and wherein the longitudinal axes of the first and second extending segments are substantially parallel.

The first plate may comprise a length, and wherein the length of the first plate is from about 10 mm to about 140 mm. The first carriage block may comprise a length, and wherein the length of the first carriage block is from about 5 mm to about 20 mm.

Another embodiment of a translational bone fixation assembly is described, comprising: a first plate having a plurality of fixation holes and a longitudinal axis; and at least a first carriage block having a plurality of fixation holes, at least a portion of the first carriage block slidably associated with at least a portion of the first plate; wherein the first carriage block is translatable in the direction of the longitudinal axis when the assembly is attached to at least one bone segment.

The assembly may further comprise a second carriage block slidably associated with at least a portion of the first plate. The second carriage block may be slidable independent of the first carriage block. The second carriage block may comprise a plurality of fixation holes.

The first and second carriage blocks may be permitted to slide simultaneously. The first carriage block may have a range of motion greater than that of the second carriage block. The range of motion of the second carriage block may be limited by a motion-limiting element. The first carriage block may be permitted to slide from about 0 mm to about 4 mm relative to the first plate.

The first plate further may comprise a bore, and wherein an extension element extends through the bore. The extension element may be able to stop the sliding movement of the first carriage block. The extension element may be permanently attached to the first plate.

Another embodiment of a translational bone fixation assembly is described, comprising: a first plate having a plurality of fixation holes and a longitudinal axis; and at least a first carriage block having a plurality of fixation holes, at least a portion of the first carriage block slidably associated with at least a portion of the first plate; wherein the first carriage block is translatable in the direction of the longitudinal axis under a coaxial force of at least about 50 grams.

The assembly may further comprise a second carriage block slidably associated with at least a portion of the first plate. The second carriage block may be slidable independent of the first carriage block. The second carriage block may comprise a plurality of fixation holes.

The first and second carriage blocks may be permitted to slide simultaneously. The first carriage block may have a range of motion greater than that of the second carriage block. The range of motion of the second carriage block may be limited by a motion-limiting element. The first carriage block may be permitted to slide from about 0 mm to about 10 mm relative to the first plate.

A method of securing at least two bone elements is described, comprising the steps of: (a) providing a translatable bone fixation assembly having a first plate having a plurality of fixation holes and a longitudinal axis, and a first carriage block having a plurality of fixation holes, wherein the carriage block is slidably associated with the first plate; (b) inserting at least one fastener through at least one fixation hole in the first plate and into a first bone element; (c) inserting at least one fastener through at least one fixation hole in the first carriage block and into a second bone element; and (d) permitting the carriage block to slide in the direction of the longitudinal axis after implantation of the bone fixation assembly.

The assembly may further comprise a second carriage block slidably associated with the first plate, and wherein the second carriage block has a plurality of fixation holes. The method may further comprise the step, inserted before step (d), of inserting at least one fastener through at least one fixation hole in the second carriage block and into a third bone element.

The third and second bone elements may be separated by the first bone element.

The method may further comprise the step of inserting applying a motion-limiting element to limit the motion of the first carriage block. The method may further comprise the step, inserted before step (b), of drilling at least one hole in at least one bone element in a location of desired fastener insertion.

The first and second bone elements may be adjacent vertebrae.

The method may further comprise the step of inserting an intervertebral spacer between the first and second bone elements.

A kit for use with bone fixation procedures is also described, comprising: at least a first plate having a plurality of fixation holes and a longitudinal axis; at least a first carriage block having a plurality of fixation holes, at least a portion of the first carriage block slidably associated with at least a portion of a first plate; wherein the first carriage block is translatable in the direction of the longitudinal axis when the assembly is attached to at least one bone segment.

The kit may further comprise at a first fastener for use with at least one fixation hole. The kit may further comprise a second fastener for use with at least one fixation hole, wherein the first fastener is substantially different than the second fastener.

The kit may further comprise a second plate and a second carriage block. The first carriage block may be slidably associated with the second plate. The second carriage block may be slidably associated with the first plate. The first and second carriage blocks may be able to be simultaneously slidably associated with the first plate.

The kit may further comprise at least one motion-limiting element for use with a carriage block. The kit may further comprise at least one temporary attachment element. The kit may further comprising at least one drill guide, and/or at least one drill.

At least a portion of the first plate slidingly engaged with the first carriage block is a dovetail portion, wherein at least a portion of the dovetail may be deformed to limit the translational motion of the first carriage block.

BRIEF DESCRIPTION OF THE DRAWINGS

While preferred features of the present invention may be disclosed in the accompanying illustrative, exemplary drawings, for the purposes of description, the invention as defined by the claims should be in no way limited to such preferred features or illustrative and exemplary drawings, wherein:

FIG. 1f is a top view of an embodiment of the carriage block of FIG. 1a;

FIG. 2a is a side view of an exemplary bone fastener for use with the plate of FIG. 1a;

FIG. 2b is a top view of an exemplary retention clip for use with the plate of FIG. 1a;

FIG. 3c is a partial top view of the plate of FIG. 3a;

FIG. 4b is a top view of the slotted bone screw hole of FIG. 4a;

FIG. 5c is a perspective view of a two-piece internal carriage block that may be used with the plate of FIG. 5a;

FIG. 8g is a top view of an alternative carriage block design for use with the track-plate of FIG. 8a;

FIG. 17b is a perspective view of the plate of FIG. 17a in a partially compressed condition.

DETAILED DESCRIPTION OF THE PREFERRED EMBODIMENTS

The plates described herein may be used in spinal fusion procedures in which a damaged or diseased disc (or part of a disc) is removed from between a pair of vertebrae and a spinal fusion spacer is placed between the vertebrae. The plates may be applied to an anterior portion of the affected vertebrae to span the affected disc space, and may be fixed to the vertebrae using bone screws. The plate may function to maintain the vertebrae aligned during the initial period following fixation in which fusion of the spacer to the adjacent vertebrae occurs. The plate may also function to share some of the axial spinal load applied to the fusion spacer to prevent extreme subsidence of the spacer into the vertebral body, such as where the patient has poor bone quality. The plates may also act to prevent the spacer from being expelled from the disc space during the initial post-operative period.

The plates may be used for single level (i.e. one-disc) or multiple-level (i.e. multiple disc) fusion procedures. Some embodiments may be used for corpectomy procedures, in which at least a portion of a vertebral body is removed. Single level plates generally may have two pairs of bone screw holes, while the multi-level plates generally may have three or more pairs of holes. While the plates herein are described with reference and application to the spine, it will be appreciated that features of the plates and the plates may have other applications, and can be applied to other bones and/or parts of the skeleton.

Figure 1A:
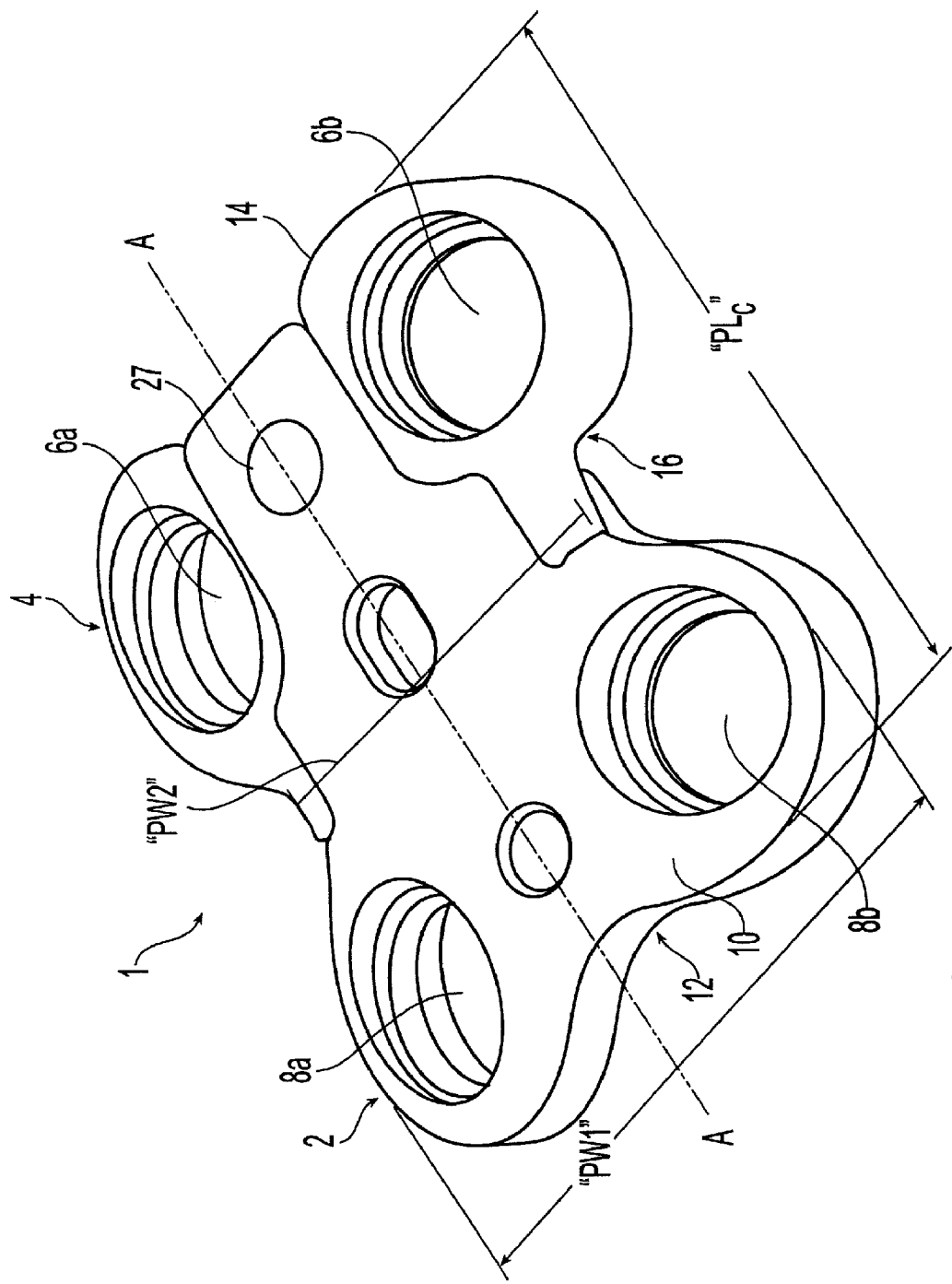
FIG. 1a is a perspective view of an embodiment of a translational spinal plate in a fully compressed configuration.
Figure 1B:
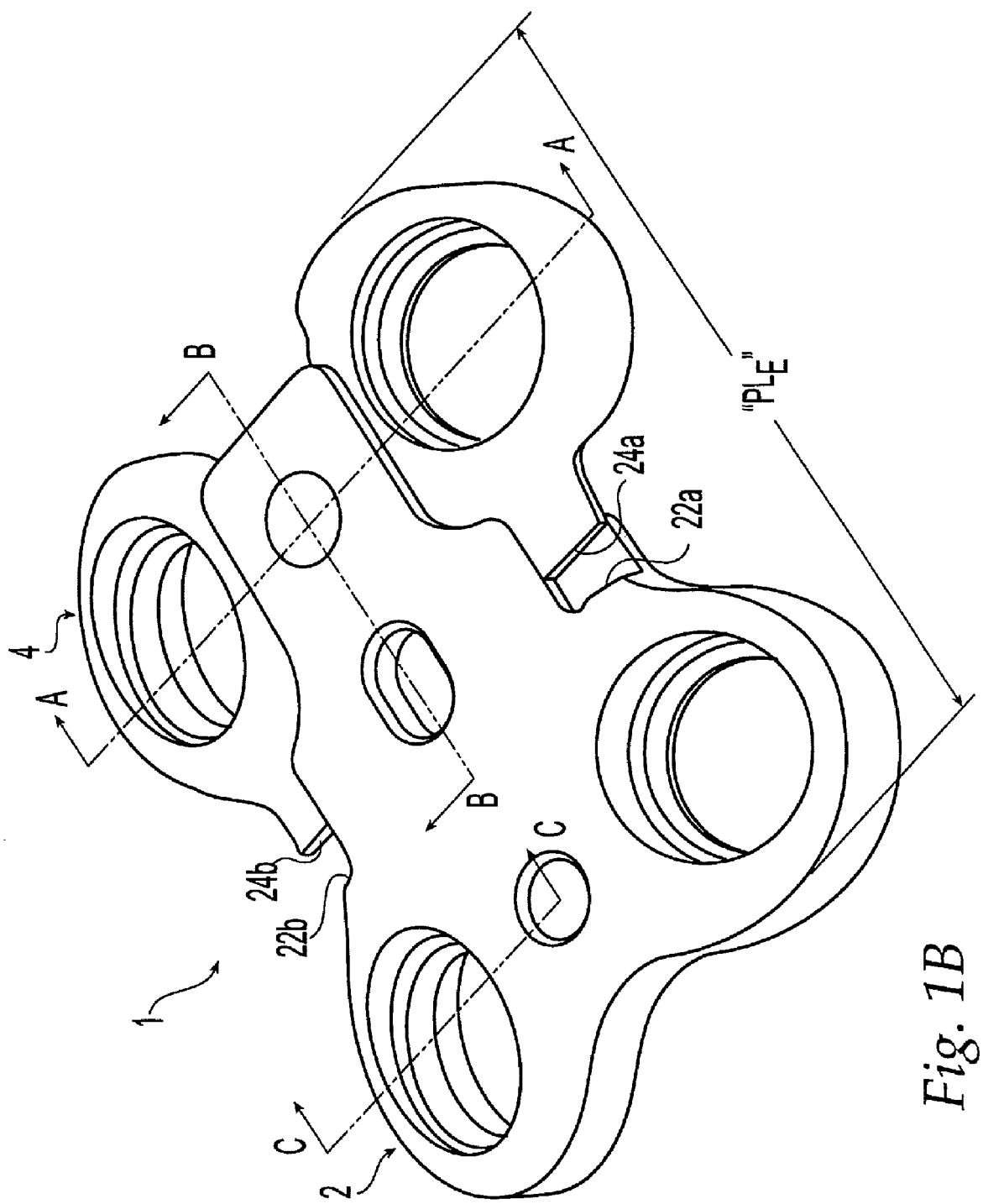
FIG. 1b is a perspective view of the plate of FIG. 1a in a fully extended configuration.

FIG. 1a shows a translating spinal fixation plate 1 for use in a single-level fusion procedure in which first plate segment 2 and carriage block 4 are configured to be fixed to first and second vertebra so that the plate 1 spans the disc space between the vertebrae. The plate 1 may have a longitudinal axis A-A and the first plate segment 2 and carriage block 4 may each have one or more bone fastener hole(s) 6, 8 for receiving a bone fastener 40 to fix the respective plate segment and carriage block to the associated vertebral body. The first plate segment 2 may have upper and lower surfaces 10, 12, while carriage block 4 may have upper and lower surfaces 14, 16. The lower surfaces 12, 16 may be configured to engage a portion of a respective vertebral body. In the illustrated embodiment, the first plate segment 2 and carriage block 4 are configured to be fixed to the anterior surfaces of a pair of adjacent vertebra. FIG. 1f shows a top view of the carriage block 4 in more detail, and FIG. 1g shows a front view of the same.

As illustrated in FIGS. 1b-1e, the first plate segment 2 may have respective translating surfaces 18a, 18b, while the carriage block 4 may have respective translating surfaces 20a, 20b configured to allow the segment and carriage block to slide toward (or away from) each another along the longitudinal axis A-A of the plate 1. The plate 1 may have an initial length "$PL_E$" sufficient to span the disc space and to allow fixation of a plate segment 2 and carriage block 4 to each vertebra.

Figure 1C:
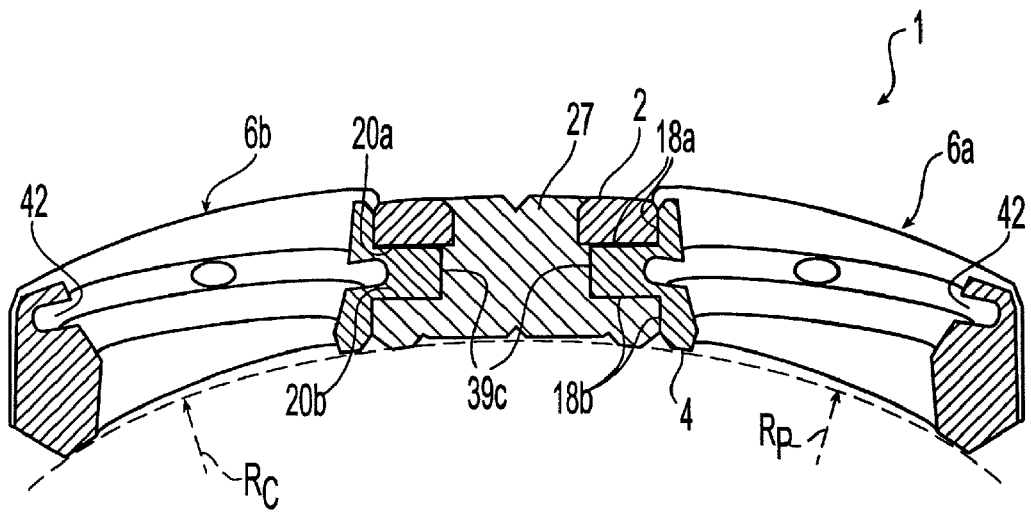
FIG. 1c is a cross-sectional view of the plate of FIG. 1b, taken along line A-A.
Figure 1D:
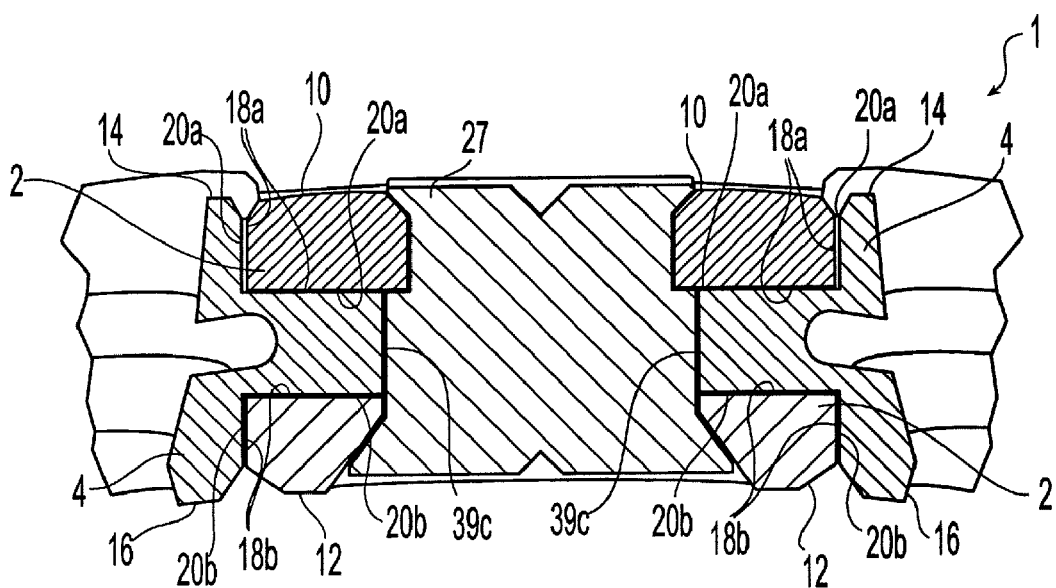
FIG. 1d is an enlarged partial cross-sectional view of the plate of FIG. 1b taken along the line A-A.
Figure 1E:
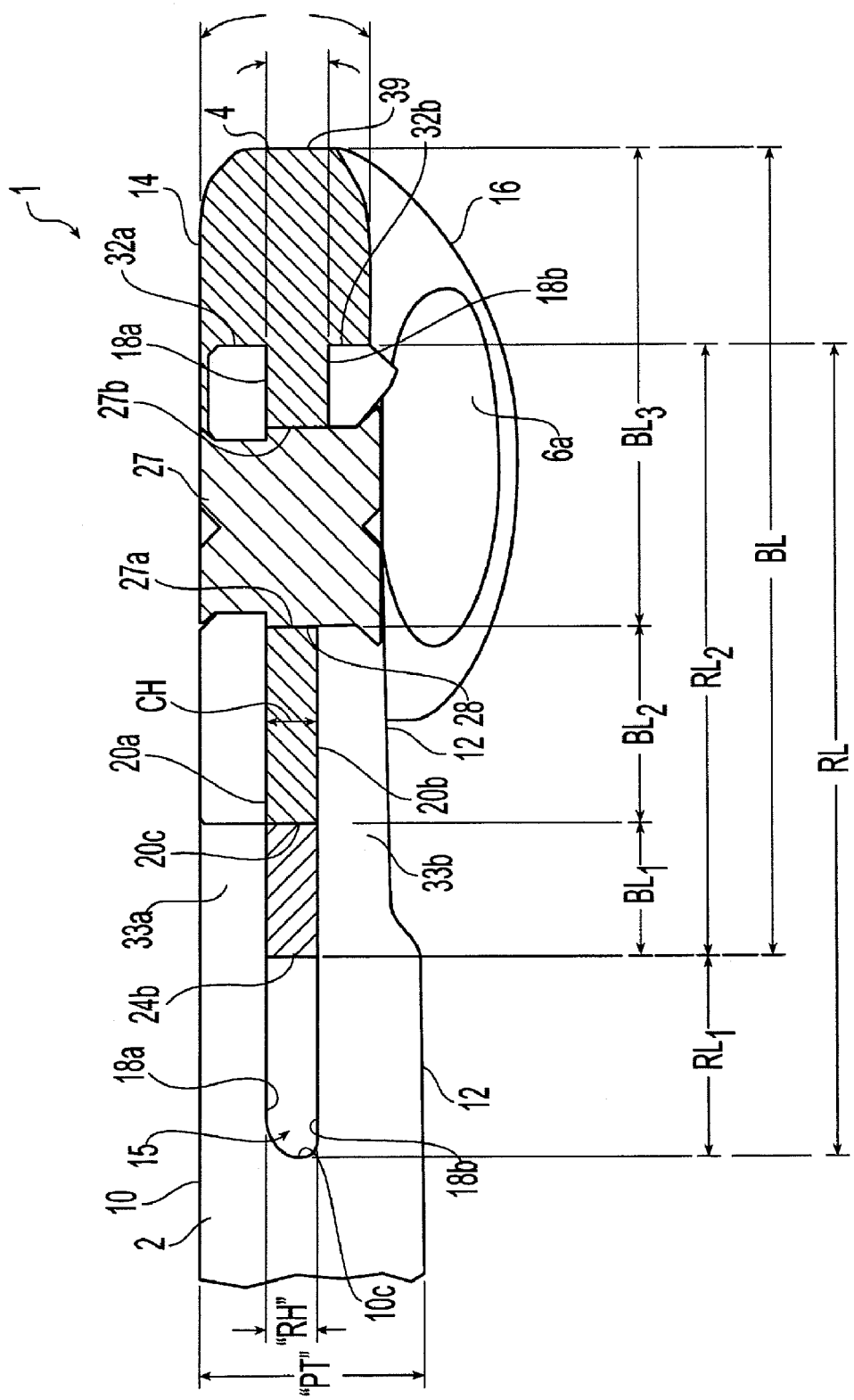
FIG. 1e is a partial elevation view of the plate of FIG. 1b, taken along line B-B.
Figure 1F:
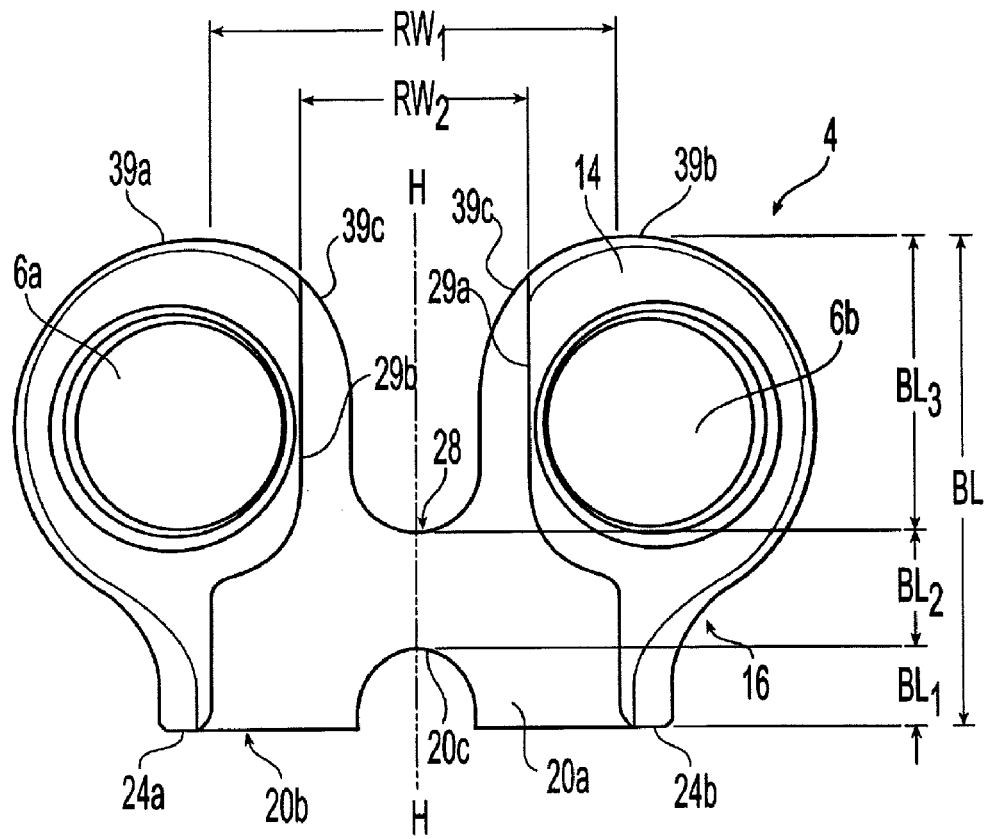
Figure 1G:
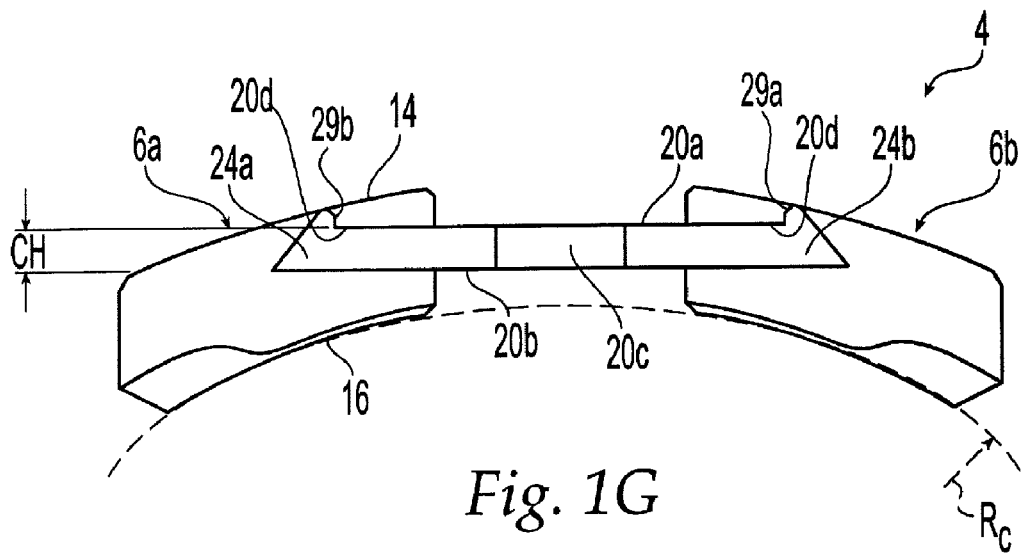
FIG. 1g is a front view of the carriage block of FIG. 1f.

The translating surfaces are illustrated in more detail in FIGS. 1c-1e, in which the respective translating surfaces are configured and dimensioned to cooperate to allow the first plate segment 2 and carriage block 4 to slide with respect to each other, while maintaining the desired structural integrity of the plate 1 in bending and torsion. Thus, when the first plate segment 2 and carriage block 4 are fixed to respective adjacent vertebrae using bone fasteners, subsequent movement of the vertebrae along the axis of the spine (e.g. due to subsidence of the intervertebral spacer into the end plates of the associated vertebral bodies) may cause the first plate segment 2 and carriage block 4 to slide together along the longitudinal axis A-A, reducing the length "$PL_C$" of the plate 1. Preferably the plate segment 2 and the carriage block 4 will move in an amount equal to the amount of subsidence of the spacer into the adjacent vertebrae.

The translation of the carriage block 4 with respect to the first plate segment 2 is contemplated and preferably provided by spinal fixation plate 1 after it has been implanted into the body. Such translation may be urged by, for example, forces within the spinal column that may directly bear upon fasteners inserted into fastener holes 6, 8 of first plate segment 2 and carriage block 4. When a translating force acts in situ upon the first plate segment 2 and/or the carriage block 4, translating surface 20a may translate relative to translating surface 18a, or vice versa. Likewise, translating surface 18b may translate relative to translating surface 20b, or vice versa. As described in more detail below, the respective pairs of translating surfaces 18a, 20a and 18b, 20b may or may not contact each other during the translation of the carriage block 4 relative to the first plate segment 2. Moreover, any of all of translating surfaces 18a, 18b, 20a, 20b may be angled, or for example, roughened, to produce a desired contact and/or resistance to translation between the respective pairs of translating surfaces 18a, 20a and 18b, 20b. Such variations are also described in more detail below.

The first plate segment 2 and carriage block 4 may also have respective compression stop surfaces 22a, 22b; 24a, 24b that may engage each other when the plate is in the fully compressed condition (see FIG. 1a). The first plate segment 2 and carriage block 4 may further have respective extension stop surfaces, 27a, 28 (see FIG. 1e) that may engage each other when the plate is in the fully extended condition (see FIG. 1b). The first extension stop surface 27a may take the form of an extension member 27, such as, for example, a rivet, pin, screw or other suitable extension disposed in a bore 30 in the first plate segment 2. The second extension stop surface 28 may comprise an end surface of the second plate segment 4. The second extension stop surface 28 may at least partially conform to the shape of the first extension stop surface 27a. The extension member 27 may be removably attached to the first plate segment 2 to allow substitution of different-sized or different styled carriage blocks 4 may be permanently fixed to the first plate assembly to capture the carriage block 4 and prevent disassembly. When the plate 1 is assembled, the first plate segment 2 and carriage block 4 may slide between the fully extended and fully compressed conditions, the amount of compression (or extension) of the plate may be limited by the arrangement of the stop surfaces. It will be recognized that the plate 1, and particularly the first plate segment 2 and the carriage block 4 may employ other stop surfaces to limit the amount of travel of the carriage block 4 with response to the first plate segment 2.

The plate segments and carriage blocks may each have a first width "PW1" corresponding to the dimension transverse to the longitudinal axis as measured across the portion of the plate having the bone fastener holes 6a, 6b, 8a, 8b. The first plate segment 2 and carriage block 4 further may have a second width "PW2" as measured across the portion of the respective segment that does not contain the bone fastener holes. The first width PW1 may be about 10 mm to about 60 mm, while the second width PW2 may be about 6 mm to about 56 mm. The first plate segment 2 and carriage block 4 may have specialized widths for spinal applications. For example, for assemblies used in the cervical region, PW1 may be from about 10 mm to about 20 mm and PW2 may be from about 6 mm to about 20 mm. Also, for assemblies used in the thorcolumbar region, PW1 may be from about 16 mm to about 30 mm and PW2 may be from about 10 mm to about 30 mm. Further, for assemblies used in the lumbar region, PW1 may be from about 20 mm to about 60 mm and PW2 may be from about 16 mm to about 60 mm. The first plate segment 2 and carriage block 4 may each have a thickness "PT" which may be about 1 mm to about 10 mm, and more preferably from about 2 mm to about 4 mm.

In the fully compressed condition, the plate length PL may be from about 10 mm to about 138 mm, and in the fully extended condition the plate length PL may be from about 12 mm to about 140 mm. The compressed and extended lengths may vary depending on the size of the patient, the region of the spine in which the plate is used. Thus, larger sizes may be used for lumbar spine applications in larger patients, while smaller sizes may be used for cervical spine applications in small patients.

The plate 1 may be curved to more naturally conform the plate to the normal anatomical curvature of the spinal column. Thus, when used in the cervical and lumbar spine, the plate may have a lordosed, or convex shape. When used in the thoracic spine, the plate may have a kyphosed, or concave shape. Alternatively, the plate may be provided in a flat configuration to fit to a lateral portion of the spine. The first plate segment 2 and carriage block 4, and in particular their lower surface 12, 16, may also be provided with a lateral curvature allowing them to closely conform to individual vertebral elements. For example, as seen in FIGS. 1c-1g, carriage block 4 may have a radius $R_C$ along its lower surface 16, and the first plate segment 2 may have a radius $R_P$ along its lower surface 12. Radius $R_C$ may be from about 10 mm to about 60 mm, and radius $R_P$ may be from about 10 mm to about 60 mm. The first plate segment 2 and carriage block 4 may also be bendable to allow the surgeon to modify the plate curvature as desired to customize the plate to the anatomy of an individual patient.

The lower surfaces 12, 16 of the first plate segment 2 and carriage block 4 may be roughened to enhance engagement between the plate and the associated vertebral body. Such roughening may be achieved by bead blasting the surfaces 12, 16 by machining ridges, grooves, or other surface profiles or projections into the surfaces, or by applying a roughening material to the lower surfaces.

FIGS. 1c-1e illustrate translating surfaces 18, 20 of plate 1 configured to provide a compression-resisting force that varies with the amount of translation between the first plate segment 2 and carriage block 4. As shown, the first plate segment 2 has upper and lower extending segments 33a, 33b each having a translating surface 18a, 18b configured to slidably engage the surfaces 20a, 20b of the carriage block 4. As shown in FIG. 1e, the translating surfaces 18a, 18b of the first plate segment 2 may form an angle α with respect to each other so that as the carriage block 4 moves, the carriage block 4 wedges against the translating surfaces 18a, 18b of the first plate segment 2 thus providing a force that increasingly opposes movement of the carriage block 4 as the carriage block 4 travels toward the vertex of angle α. In the embodiment shown in FIG. 1e, angle α is slightly divergent. Alternatively, however, angle α may be convergent, such that surfaces 18a, 18b of the carriage block 4 may encounter more friction as carriage block 4 translates toward the first and second ends 32a, 32b of the first and second extending segments 33a, 33b of first plate segment 2. Moreover, angle α may not exist at all if surfaces 18a, 18b are substantially parallel. This may be preferable in light of the fitting and contouring options discussed below. All of these designs may be useful in preventing extreme subsidence of the associated intervertebral spacer. The wedge angle α may be from about 1 degrees to about 10 degrees, and may generally correspond to variances in the recess height RH along the longitudinal axis of the first plate segment 2. Moreover, the translating surfaces of the first plate segment 2 and carriage block 4 surfaces may be provided with ratchet teeth, grooves, roughened portions, or other surface features to provide the desired increased resistance to compression. Further, the carriage block 4 may be slightly oversized in relation to the sliding area provided by the first plate segment 2, so as to create a frictional fit, but still allowing translation of the carriage block 4 while engaging the first plate segment 2.

As further shown in FIG. 1e, upper and lower surfaces 10, 12 of the first plate segment 2 may also form an angle β with respect to each other. Angle β may be substantially the same as wedge angle α, discussed above. As with angle α, angle β may be convergent, divergent, or not exist at all if upper and lower surfaces 10, 12 are substantially parallel. It is contemplated that any combination of suitable angles α and β may be formed on a single plate segment, such as first plate segment 2. Moreover, angle β may generally correspond to variances in the plate thickness PT along the longitudinal axis of the first plate segment 2.

The wedge angle α may be formed with a variety of arrangements and/or techniques. First, the translating surfaces 18a, 18b and/or 20a, 20b could be machined to create the wedge angle α. Alternatively, the segments 33a, 33b could be bent and held at a certain distance that would create the wedge angle α, which would create the desired frictional fit between the carriage block 4 and the first plate segment 2 to achieve the desired control of movement between the carriage block 4 and the first plate segment 2 after implantation into the body. A preferred exemplary plate may require about 50 grams to about 1600 grams of force to move the carriage block 4 relative to the first plate segment. More specifically, an exemplary, illustrative plate for cervical applications may require about 50 grams to about 400 grams, and more preferably about 180 to about 220 grams. An exemplary, illustrative plate for lumbar and thorcolumbar applications may require about 100 grams to about 1600 grams, and more preferably about 400 grams to about 800 grams. The first plate segment 2 and carriage block 4 may also be designed so that the carriage block moves relatively freely with little or no friction.

FIG. 1e also shows relevant distances of the translating first plate segment 2 and carriage block 4. As viewed from the side, the translating upper and lower surfaces 18a, 18b, and side surface 18c of the first plate segment 2 may form a cavity 15 within the first plate segment 2. The cavity 15 has a total length "RL", and a recess height "RH". As viewed from the side, the carriage block 4 has a total length "BL" which extends, in this embodiment, from stop surface 24b to carriage block end 39. Carriage block also has an translating carriage height "CH". The portion of the recess engaging the carriage block 4 is defined by length $RL_2$, while the remaining portion of the recess left void has a length $RL_1$. It is seen that carriage block 4 has a side surface 20c from this perspective. The portion of the carriage block 4 that extends outwardly from the side surface 20c to the stop surface 24b has a length $BL_1$. The portion of the carriage block 4 has extends inwardly from the side surface 20c to the first extension stop surface 27a has a length $BL_2$. The remainder of the carriage block 4 has a length $BL_3$. Therefore, the translating relationship between the carriage block 4 and first plate segment 2 can be described as follows: as carriage block 4 slides into cavity 15 of first plate segment 2, $BL_2$ and $RL_2$ may increase, and $BL_3$ and $RL_1$ may consequently decrease. The aforementioned distances may bear any relationship that is suitable for creating the desired spatial relationship of the first plate segment 2 and carriage block 4, and the dimensional preferences of the components therein.

FIGS. 1f-1g show a carriage block 4 in more detail. FIG. 1f shows a carriage block from a top view, while FIG. 1g shows a carriage block 4 from a front view. Lengths BL, $BL_1$, $BL_2$, and $BL_3$ are shown, and may correspond to the discussion above in reference to FIG. 1e. Likewise, the translating height CH of carriage block 4 is shown, and may similarly correspond to the discussion above in reference to FIG. 1e. Carriage block 4 may have two ends 39a, 39b near fastener holes 6a, 6b. Carriage block 4 also may have ridges 29a, 29b along the upper surface 14. Ridges 29a, 29b may partially define the boundaries of the translating surface 20a of the carriage block 4, and may vary in width along the longitudinal axis H-H of carriage block 4. Specifically, ridges 29a, 29b may span a first width $RW_1$ and a second width $RW_2$. First width $RW_1$ may generally correspond to the upper surface 10 of first plate segment 2 near the stop surfaces 24a, 24b (see, e.g., FIGS. 1a-1b). Second width $RW_2$ may generally correspond to the dimensions of the first plate segment 2 near its extending segments 33a, 33b (see, e.g., FIG. 1e).

Ridges 29a, 29b may also form angled portions 20d of the upper translating surface 20a. Such angled portions 20d may be utilized to engage an upper extending segment 33a of a first plate segment 2 during translation. The configuration of the respective translating surfaces 18a, 20a, and 20d thus may operate to retain the carriage block 4 in close engagement with the first plate segment 2, facilitating movement of the block 4 along the longitudinal axis A-A as previously described. It is contemplated, however, that other features may be used to gain the benefits of ridges 29a, 29b and angled portions 20d, such as grooves, notches, teeth, or other suitable retention or alignment designs.

Carriage block 4 may also have a curved surface 39c between ends 39a, 39b, and curved surface 39c may include second extension stop surface 28. In use, curved surface 39c and second extension stop surface 28 may engage the side surfaces 27a, 27b of an extension member 27. When the plate 1 is in its compressed state, as shown in FIG. 1a, the extension member 27 may be adjacent to second extension stop surface 28. A detailed view of this arrangement is also shown in FIG. 1e, discussed supra, wherein first extension stop surface 27a abuts second extension stop surface 28. As carriage block 4 translates from the compressed position, curved surface 39c may engage the side surfaces of extension member 27. The relationship between curved surface 39c and extension member 27 is also shown in FIG. 1c.

FIG. 1c also shows an exemplary fastener screw hole 6a, 6b configured to receive a retention clip 38 to engage an associated bone fastener 40 to prevent back-out of the fastener during use. Clip 38 (see FIG. 2b) resides at least partially within a circumferential groove 42 in the bone fastener hole 6a, 6b, so that a portion of the clip 38 protrudes into the bone fastener hole 6a, 6b. The clip 38 is configured to engage a circumferential groove 44 in the head 46 of the bone fastener 40 (see FIG. 2a) when the fastener is placed in the hole 6a, 6b and driven into the underlying bone. It should be noted that fastener holes 8a, 8b may exhibit all or some of the same characteristics as fastener holes 6a, 6b.

Figure 2A:
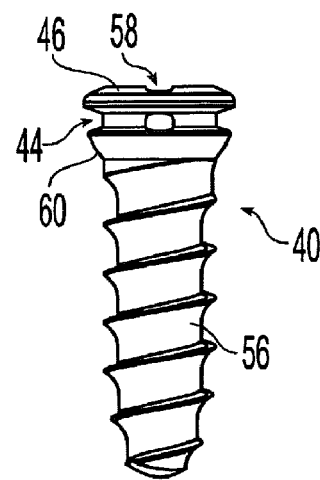
Figure 2B:
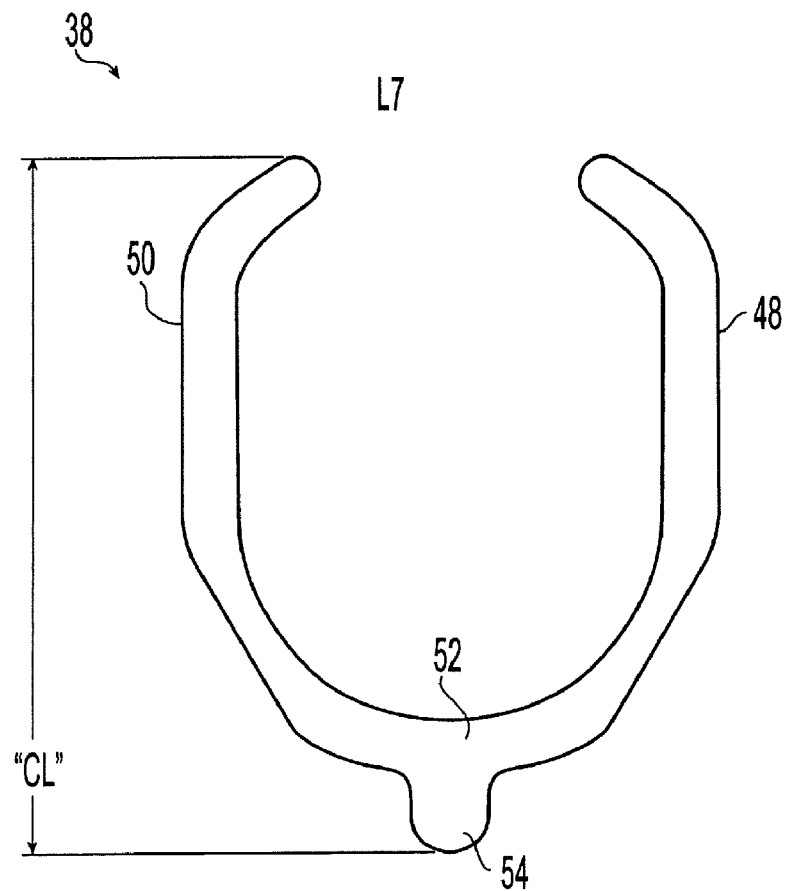

FIG. 2b shows an exemplary retention clip 38 having a generally wishbone shape. The clip 38 may have generally parallel arms 48, 50 and a connecting portion 52 that may permit elastic expansion/compression of the arms that allow the clip arms 48, 50 to expand when the bone fastener 40 is inserted, and to contract when the clip 38 engages the groove 44 in the fastener head 40. The clip may have a length "CL" The clip 38 may further have an aligning projection 54 that extends from connecting portion 52 in a direction opposite that of the arms 48, 50. The aligning projection 54 may be received within a corresponding recess (not shown) in the plate 1 to maintain the clip 38 in a desired orientation with respect to the plate 1. While carriage block 4 has been illustrated and described as having a pair of bone fastener holes 6a, 6b, carriage block 4 may have a single bone fastener hole, three bone fastener holes (as shown in FIG. 8g, discussed infra), or any number of bone fastener holes. Likewise, while first bone plate segment 2 has been illustrated and described with a pair of bone fastener holes 8a, 8b, first bone plate segment 2 may have a single bone fasteners hole, three bone fastener holes or any number of bone fastener holes.

FIG. 2a illustrates an exemplary fastener 40 for use in fixing the plate 1 to the targeted vertebral bodies. The illustrated fastener 40 is a bone screw having a head portion 46 and a threaded shank portion 56. The head portion 46 may have a drive recess 58 configured to receive a driving tool, and a circumferential groove 44 configured to receive a portion of the previously-described retention clip 38. The head portion 46 may have an angled underside 60 configured to facilitate expansion of the retention clip 38 when the fastener is inserted into the associated bone fastener hole 6, 8 and driven into bone. When the fastener head 46 passes far enough through the hole, the clip 38 snaps back into the groove in the head 46, thus capturing the screw head within the hole 6, 8.

Further details and embodiments of appropriate fasteners, retention clips and bone fastener hole designs may be found in co-pending U.S. non-provisional patent application Ser. No. 10/653,164 entitled "Bone Plate with Captive Clips", by Duong, et al., filed Sep. 3, 2003, the entire contents of which are incorporated by reference. It should be pointed out that while bone fastener holes 6, 8 have been described and illustrated as having a clip 38 to resist fastener back out, any number of well-known fastener holes and fasteners may be employed with bone plate 1, including bone fastener holes that are relatively smooth, partially or fully threaded, straight or conically shaped, elongated slots, with or without ramped surfaces to provide compression or combination holes that are both threaded and contain smooth ramped surfaces.

Figure 3A:
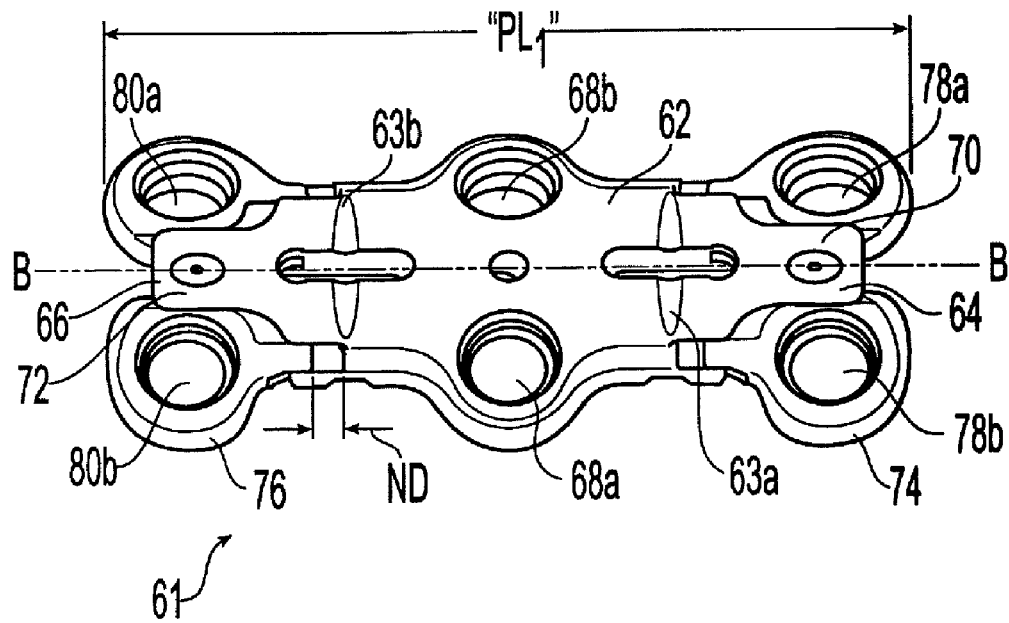
FIG. 3a is a perspective view of an embodiment of a translating spinal plate for use in a two-level spinal fusion procedure, the plate being shown in the fully extended position.

FIG. 3a shows a plate 61 that may be used in a two-level fusion procedure, and may have a fixed plate portion 62 with first and second ends 64, 66, and first and second bone fastener holes 68a, 68b disposed therebetween. The bone fastener holes 68a, 68b may be configured to receive fasteners to fix the plate portion 62 to a first vertebral body. The fixed plate portion 62 may have a longitudinal axis B-B and each of the first and second ends 64, 66 may have a carriage block engaging portion 70, 72. First and second carriage blocks 74, 76 may slidingly engage the carriage block engaging portions 70, 72 of the fixed plate portion 62 to allow the carriage blocks 74, 76 to translate with respect to the fixed plate portion 62 along the plate axis B-B. The first and second carriage blocks 74, 76 may each have bone fastener holes 78a, 78b; 80a, 80b configured to receive fasteners 40 to fix the carriage blocks to respective vertebral bodies positioned on opposite sides of the first vertebral body.

The carriage blocks 74, 76 and the respective carriage block engaging portions 70, 72 of the fixed plate portion 62 may have translation surfaces and compression and extension stop surfaces as described above in relation to the plate segment 2 and carriage block 4 of FIGS. 1a and 1b. These translation and stop surfaces may allow the carriage blocks 74, 76 to move along the longitudinal axis B-B of the fixed plate portion 62, within a predetermined range of linear translation. Thus, the translation and stop surfaces may allow the carriage blocks 74, 76 to move from a fully extended configuration (see FIG. 3a) in which the plate has a length "$PL_1$" of from about 20 mm to about 100 mm, to a fully compressed configuration (see FIG. 3b) in which the plate has a length "$PL_2$" of from about 16 mm to about 96 mm. The carriage blocks and fixed plate portion preferably may be configured provide up to 12 mm of compression between adjacent vertebrae to accommodate post-operative settling of the intervertebral spacer between the vertebral bodies. Each carriage block 74, 76 may individually move up to 6 mm with respect to the fixed plate 62.

The plate 61 may be curved to generally conform to the curvature of the portion of the spine to which it will be attached. In addition, the surgeon may wish to customize the plate to further conform to the specific anatomy of the individual patient. Thus, as illustrated in FIG. 3a, the fixed plate portion 62 may be provided with one or more bending notches 63a, 63b disposed a predetermined distance "ND" away from the translating surfaces to provide a safe location for plate bending, thus ensuring that such bending will take place in the plate portion 62, that does not contain the carriage blocks 74, 76, and thus not compromise the sliding interaction between the carriages 74, 76 and the plate portion 62. These notches 63a, 63b may be configured to be easily engaged with a standard bending tool. Notches may additionally be formed in the lower surface of plate 62, preferably opposite notches 63a, 63b on the top surface.

Figure 3B:
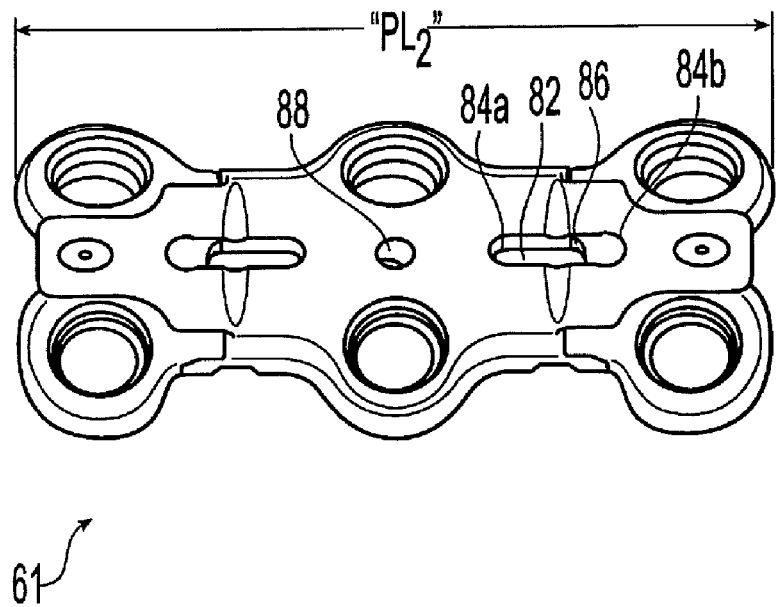
FIG. 3b is a perspective view of the plate of FIG. 3a, in the fully compressed condition.
Figure 3C:
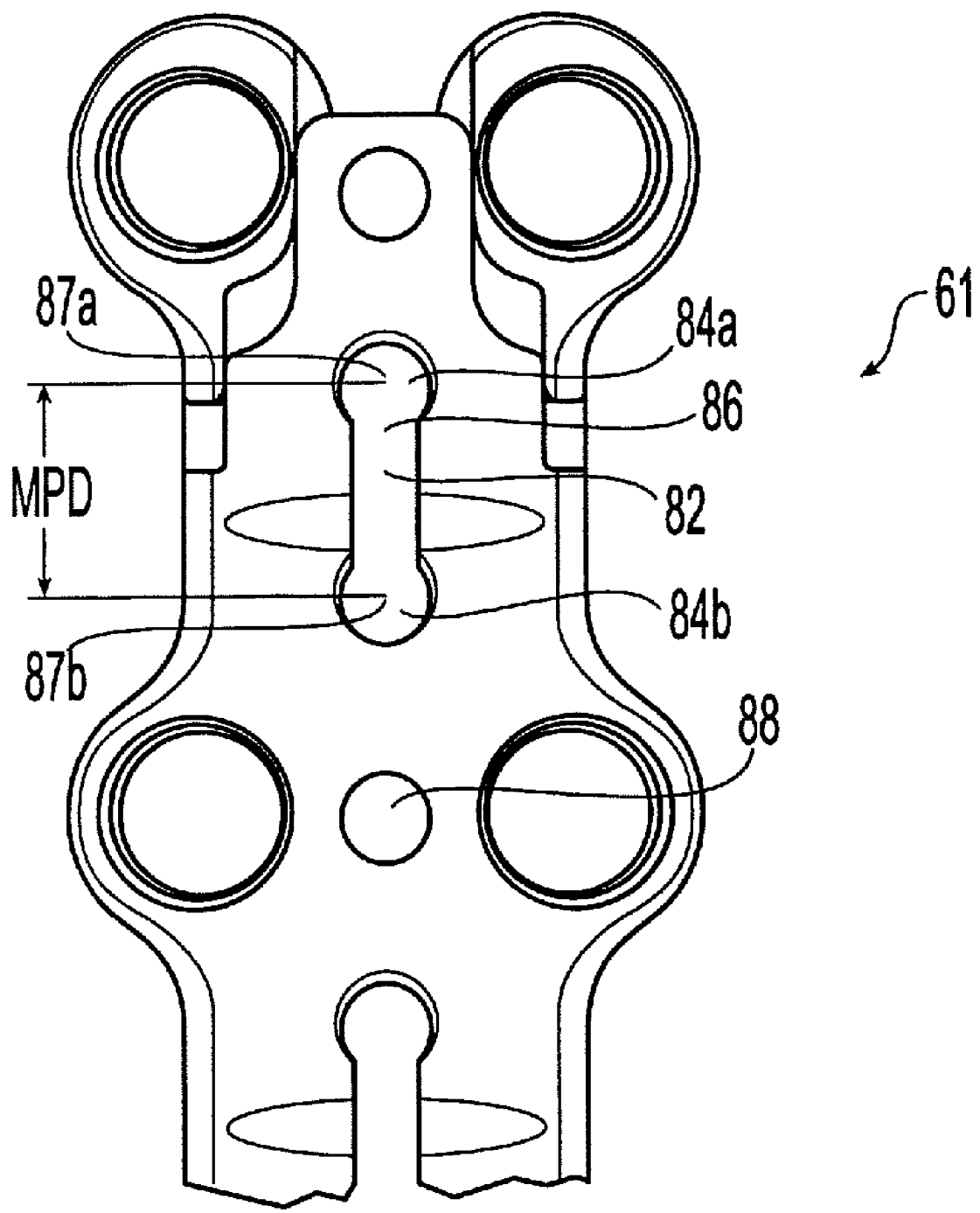

The plate 61 of FIGS. 3a-3b may have at least one recess 82 configured to receive a drill guide or other tool for pre-forming a hole in the vertebral body into which the bone screws will be inserted to fix the plate 61 to the vertebrae. In the illustrated embodiment, and as shown in detail in FIG. 3c, the recess 82 comprises a dog-bone shape having a pair of threaded holes 84a, 84b disposed at each end of a slot 86. The threaded holes 84a, 84b may each have a midpoint 87a, 87b, with a distance "MPD" between the midpoints. The distance MPD may be at least about 1 mm. The threaded holes may engage a threaded or otherwise engageable portion of a drill guide, such as those described, inter alia, in co-pending U.S. patent application Ser. Nos. 10/619,472 to Rathbun, et al., filed Jul. 16, 2003 and titled "Plating System with Multifunction Drill Guides," and Ser. No. 10/639,515 to Binder Jr. et al., filed Aug. 13, 2003 and titled "Quick-Release Drill-guide Assembly for Bone Plates", the entire contents of each application are incorporated herein.

Figure 3D:
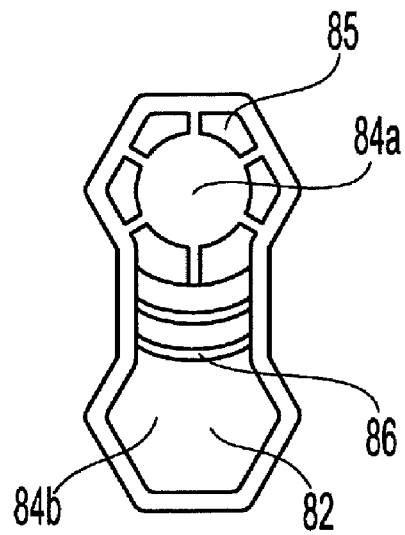
FIG. 3d is a partial top view of a hexagon-shaped recess for use with a plate.
Figure 3E:
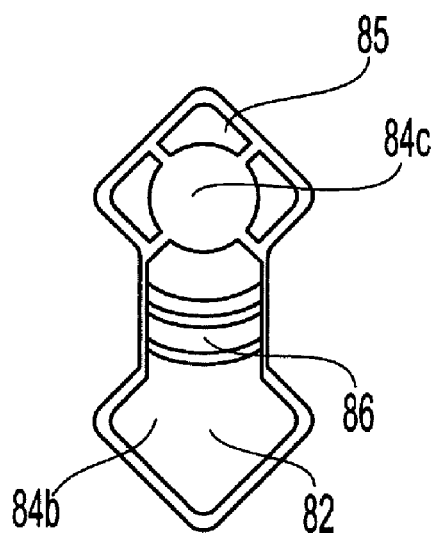
FIG. 3e is an partial top view of a square-shaped recess for use with a plate.
Figure 3F:
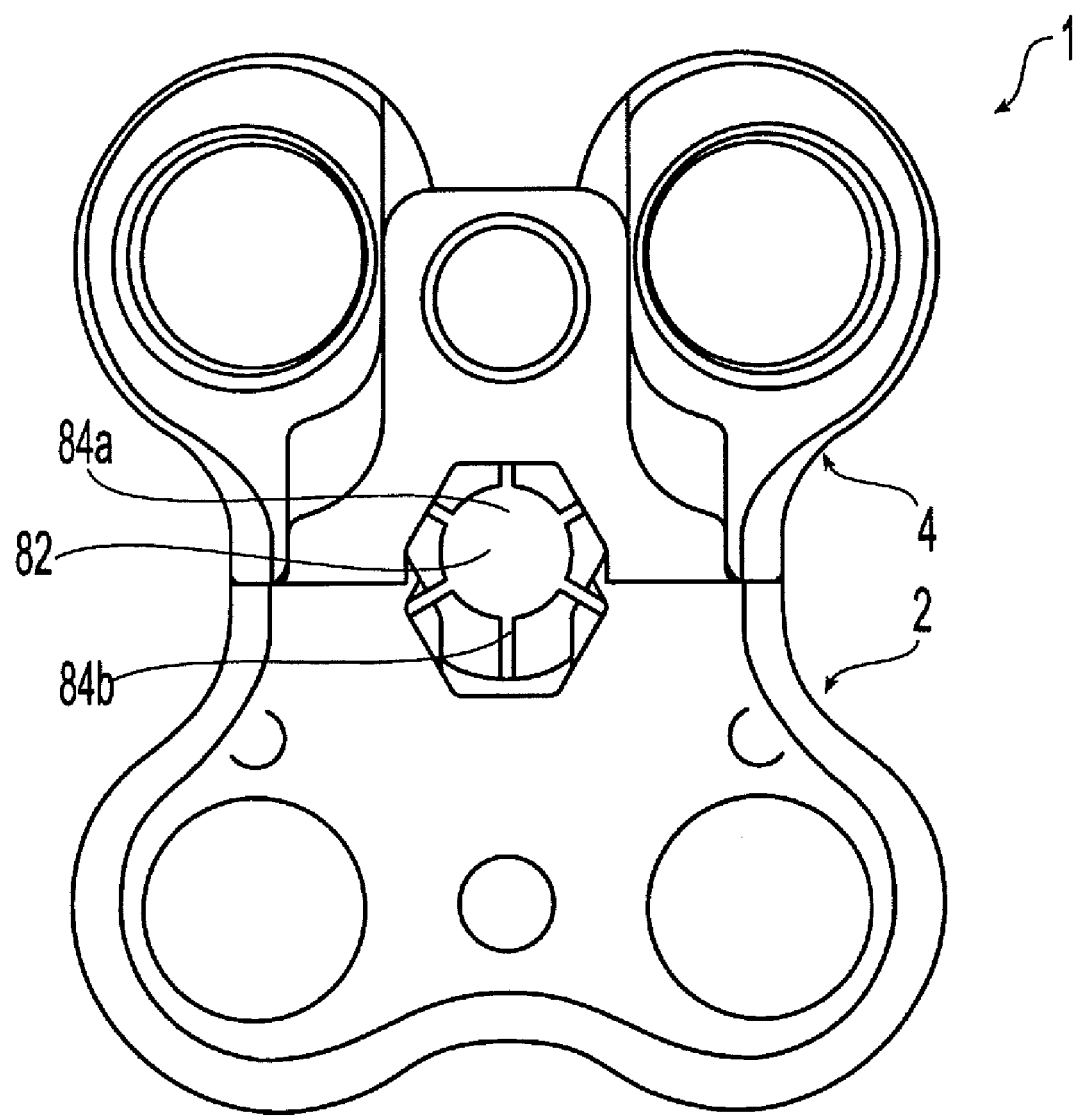
FIG. 3f is a top view of an embodiment of a translational spinal plate with an overlapping hexagonal recess.

In an alternative embodiment, the recess 82 at least partially comprises a polygonal shape, such as a hexagon, rectangle, or square. The recess 82 may also take the shape of a plurality of polygonal shapes, for example, two overlapping hexagons may comprise the shape of the recess 82 to form a combination-polygonal recess. These embodiments may be particularly useful in single-assembly plates with a reduced area in which to place a recess 82 for purposes of aligning a drill guide or similar instrumentation. An embodiment of a hexagon-shaped recess 82 is shown in FIG. 3d. While an embodiment of a square-shaped recess 82 is shown in FIG. 3e. An embodiment of a translational plate assembly utilizing an overlapping hexagon-shaped recess 82 is shown in FIG. 3f. The recess 82 may also serve a spacer-visualization function, allowing the surgeon to view the position of the intervertebral spacer after the plate 61 has been installed.

A second recess 88 may be provided adjacent recess 82 and may be configured to receive a temporary attachment pin (not shown) to temporarily fix the plate 61 to at least one vertebral body while fastener holes are being drilled in the bone. The pin may have a sharpened tip to allow easy penetration into the bone cortex, and the tip may also have threads configured to affirmatively engage the bone.

Alternatively, recess 82 may serve both the function of engaging the engageable portion of a drill guide and receiving an attachment pin, as described above. A polygonal or combination-polygonal recess 82 may be especially useful for these purposes, with the attachment pin being of the appropriate shape and size to fit snugly within at least a portion of the recess 82 and into an appropriately shaped hole in a separate plate.

Moreover, a motion-limiting shim 85 as shown in FIGS. 3d-3f, may be inserted into the recess 82, for limiting the translation of at least one plate unit during use. At least a portion of shim 85 may be shaped to fit in at least a portion of the recess 82 so that the shim 85 will not translate in the recess. Based on the shape of the recess 82, the shim 85 may be of a corresponding shape, similar to the attachment pin described above. At least a portion of the shim 85 extends down and blocks the pathway in which the carriage block moves. The recess 82 may be configured in that the shim 85 may be inserted at multiple locations so a user can adjust the amount of distance the carriage block may travel before the shim 85 would prevent further movement. The shim 85 being inserted into the top of the bone plate may be easily used and implemented during the implant procedure since the top of the plate should be readily accessible. The portion of the shim 85 that contacts the carriage block may include a cantilevered section or leaf spring that will provide increased resistance to the movement of the carriage block as the carriage block translates until it has moved a predetermined distance at which point the shim 85 may prevent any further movement of the carriage block. At least a portion of a shim 85 should also be accessible to a user, so that the shim may be removable. An alternative embodiment of a motion-limiting shim is discussed infra in FIG. 9, along with greater detail of motion-limiting shims generally. The recess 82 and 88 as well as the motion-limiting shim 85 described in reference to plate 61 and shown in FIGS. 3c-3f, optionally may each individually or in combination be incorporated into the bone plate 1 described supra.

Figure 4A:
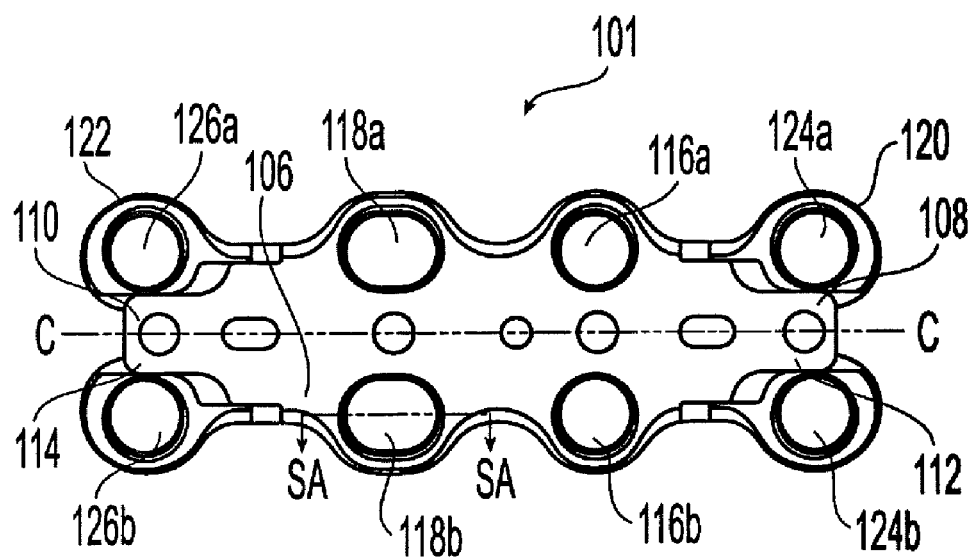
FIG. 4a is a top view of another embodiment of a translational spinal plate with a pair of slotted bone screw holes.

FIG. 4a shows a plate 101 for use in a three level fusion procedure. The plate 101 may have a fixed plate portion 106 with first and second ends 108, 110 each having a carriage block engaging portion 112, 114, and a longitudinal axis C-C. The fixed plate portion 106 may have two pairs of bone fastener holes 116a, 116b; 118a, 118b for engaging a pair of adjacent vertebrae. The first pair of bone fastener holes 116a, 116b may be round and thus may be used to rigidly fix the plate portion to the underlying vertebral body. The second pair of bone screw holes 118a, 118b may be slotted, with each hole having a slot axis "SA-SA" oriented substantially parallel to the plate axis C-C. The slotted holes 118a, 118b may have a slot length "SL" as measured from the centroid "X," "Y" of the circles that bound the ends of the holes 118a, 118b. The slot length "SL" may be from about 0.5 mm to about 10 mm.

The slotted holes 118a, 118b may be configured to allow the head 46 of an associated bone screw to translate along the slot axis SA during operation. This may allow the adjacent vertebral bodies to translate with respect to each other along the plate axis C-C after the plate 101 has been attached to the vertebra using bone fasteners 40 inserted through the round and slotted bone fastener holes 116a, 116b; 118a, 118b. Thus, the slot length SL may be dimensioned to allow a predetermined amount of translation between the vertebral bodies during operation. The slot length SL as measured between the respective centroids X, Y of the circles that define the slot ends 119a, 119b may be from about 0.5 mm to about 10 mm.

Figure 4B:
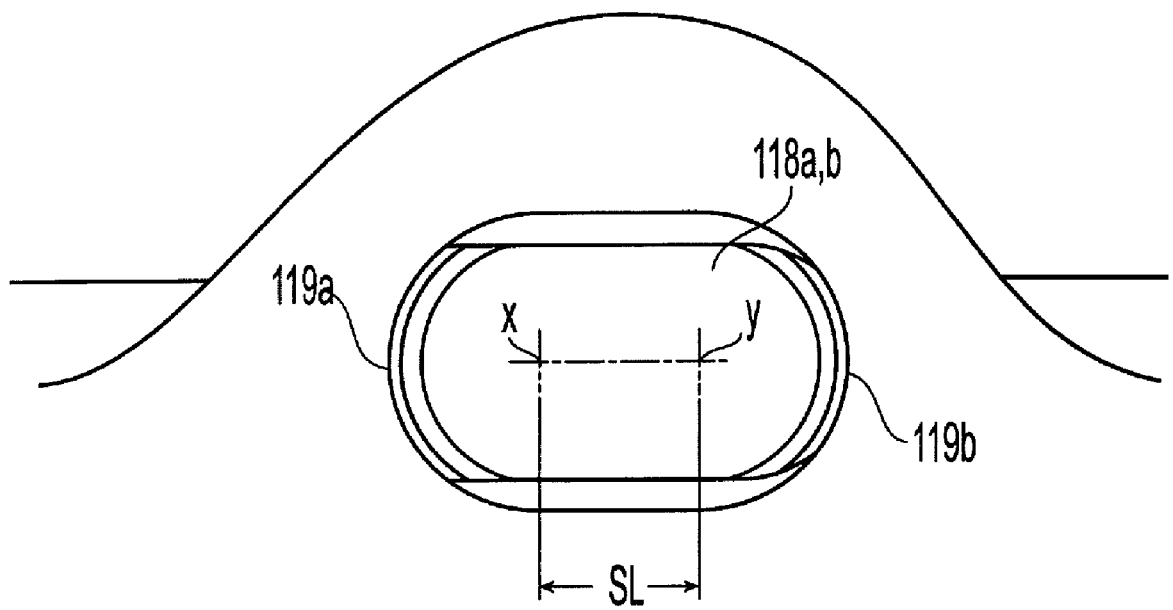

As shown in detail in FIG. 4b, the slotted holes 118a, 118b may have all the features as previously described in relation to the round holes of FIG. 1c, including appropriate features for receiving a retention clip 38 (see FIG. 2b) for securing a bone fastener 40 within the slotted hole 118a, 118b during use. Where retention clips 38 are used, the arms 48, 50 of the clips 38 may have a length "CL" sufficient to engage the groove 44 in fastener head 46 at any point along the length SL of the slotted hole 118a, 118b. Thus, the retention clip 38 may have a length CL that is greater than that of clips used in the round bone screw holes 116a, 116b.

The plate 101 of FIG. 4a may further have first and second carriage blocks 120, 122 engaged with respective first and second ends 108, 110 of the fixed plate portion 106 to allow the plate 101 to engage third and fourth vertebral bodies. The carriage blocks 120, 122 may have all of the features of the carriage blocks described above in relation to FIGS. 1a-1g and 3a-3f. Thus, each carriage block 120, 122 may have at least one bone fastener hole 124a, 124b; 126a, 126b for engaging an underlying vertebral body, and may have translating surfaces as described above in relation to FIGS. 1a-1g and 3a-3f to allow the carriage blocks 120, 122 to translate with respect to the fixed plate portion 106 along the plate axis C-C within a predetermined amount, also as previously described.

Figure 5A:
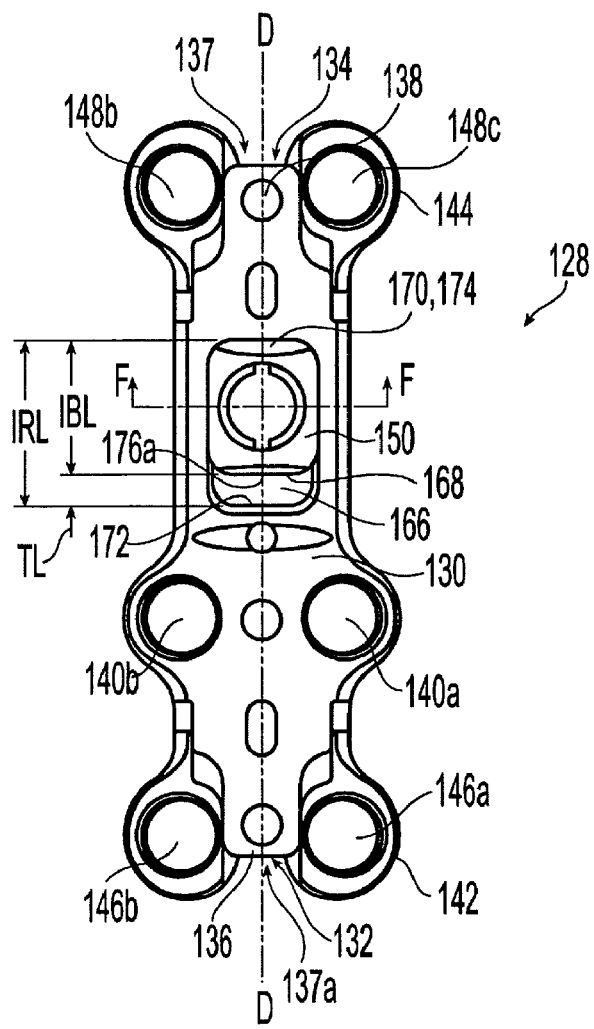
FIG. 5a is a perspective view of another embodiment of a translational spinal plate with an internal carriage block.

FIG. 5a shows a plate 128 for use in a three-level fusion procedure. The plate 128 may have a fixed plate portion 130 with first and second ends 132, 134 each having a carriage block engaging portion 136, 138, and a longitudinal axis D-D. The fixed plate portion 130 may have one pair of round bone screw holes 140a, 140b for rigidly fixing the plate portion 130 to an underlying vertebral body. The plate 128 may further have first and second end carriage blocks 142, 144 engaged with respective first and second ends 132, 134 of the fixed plate portion 130 to allow the plate 128 to translatably engage second and third vertebral bodies. The end carriage blocks 142, 144 may have any or all of the features of the carriage blocks described above in relation to the previous figures, and thus, each carriage block 142, 144 may have at least one bone fastener hole 146a, 146b; 148a, 148b for engaging an underlying vertebral body, and may have appropriate translating surfaces configured to cooperate with the first and second ends 132, 134 of the plate to allow the carriage blocks 142, 144 to translate with respect to the fixed plate portion 130 along the plate axis D-D within a predetermined range as previously described.

Figure 5B:
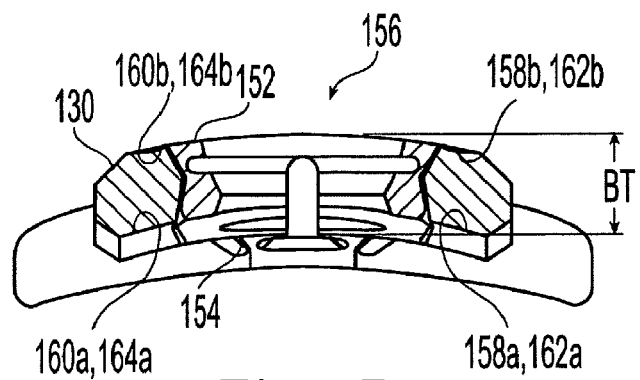
FIG. 5b is a cross-sectional view of the plate of FIG. 5a taken along the line F-F.

The plate of FIG. 5a may also have an internal carriage block 150 disposed between the bone screw holes 140a, 140b and end carriage block 144 to allow the plate to translatably engage a fourth vertebral body. As shown in greater detail in FIG. 5b, the internal carriage block 150 may have upper and lower surfaces 152, 154 and a fastener hole 156 in communication therewith. The internal carriage block 150 may further have a pair of side surfaces 158a, 158b; 160a, 160b configured to slidingly engage corresponding side surfaces 162a, 162b; 164a, 164b of a longitudinal recess 166 formed in the fixed plate portion 130. In one embodiment, the side surfaces 158a, 158b; 160a, 160b of the internal carriage block 150 may be "v"-shaped and may correspond to inverted "v"-shaped side surfaces of the recess 166. The "v"-shaped arrangement of side surfaces 158a, 158b; 160a, 160b may traverse about 90% of the thickness "BT" of the carriage block, which may impart a degree of lateral flexibility to the carriage block to allow it to be laterally compressed to "snap" it into the recess 166, which may therefore facilitate the insertion of the carriage block 150 into a recess 166. The carriage block 150 may be retained within the recess by the interaction of the corresponding side surfaces 158, 162; 160, 164. The carriage block 150 may further have compression and extension stop surfaces 168, 170 configured to engage corresponding surfaces 172, 174 of the recess 166. The internal carriage block 150 may have a length "ICL" and the recess 166 may have a length "IRL." In general, the length IRL will be greater than the length ICL to allow a the internal carriage block 150 to slide within the recess 166.

The internal carriage block 150 may slide within the recess 166 along the longitudinal axis of the plate "D-D" between the respective extension and compression stop surfaces 174, 172 of the plate 130. Length ICL may be from about 5 mm to about 20 mm, while length IRL may be from about 7 mm to about 30 mm. As noted, the lengths will be selected to provide a desired amount of translation "TL" between the carriage block and the fixed plate portion to thus accommodate a desired translation between the vertebrae attached to the fixed plate portion 130 and the internal carriage block 150. The translation may preferably be from about 5 mm to about 25 mm.

It is noted that although the illustrated embodiment comprises corresponding "v"-shaped surfaces, the side surfaces of the screw carriage and slot may assume any shape appropriate to allow the desired longitudinal sliding while preferably preventing the carriage from disengaging from the slot. Thus, dovetail surfaces, "u"-shaped surfaces, mortise-and-tenon surfaces, channels, grooves, ridges, etc. may also be used as desired.

The fastener hole 156 of the internal carriage block 150 may have all the features as previously described in relation to the round holes of FIG. 1c, or the slotted holes of FIGS. 4a-4b, including appropriate configurations for receiving a retention clip 38 (see FIG. 2b) to secure a bone fastener 44 (see FIG. 2a) within the hole 156 during use.

Figure 5C:
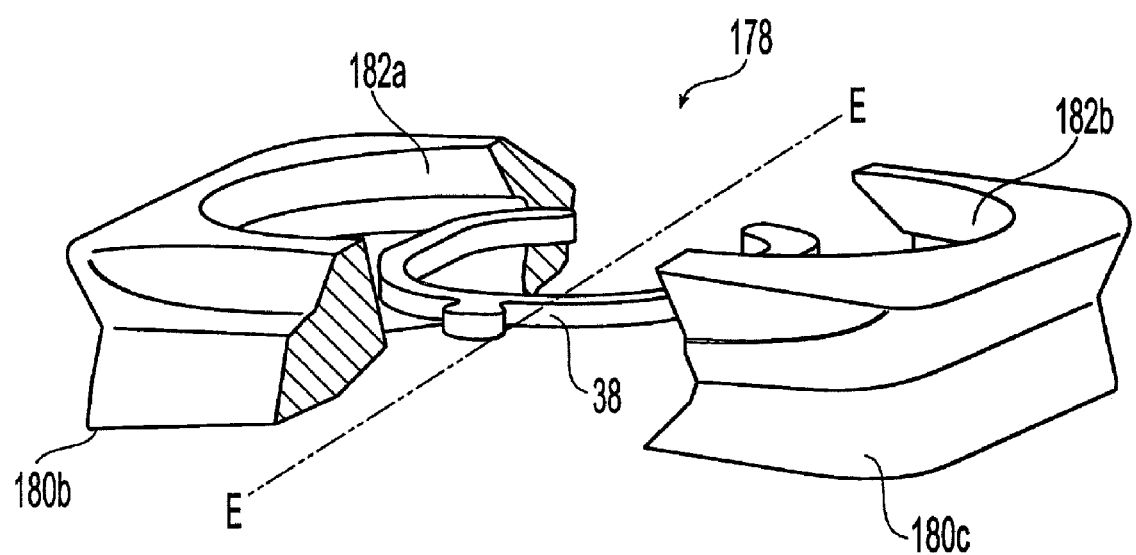

FIG. 5c shows a two-piece internal carriage block 178 that may be used with the plate 128 of FIG. 5a. The two-piece carriage block 178 may be divided substantially into halves 180a, 180b along the block longitudinal axis "E-E." The block halves 180a, 180b may be disassembled, shifted longitudinally with respect to each other, nested together, and installed within the plate recess 166 in the nested state. Once they have been installed in the recess 166, the halves 180a, 180b may be realigned and fit back together to form a unitary piece. The retention clip 38 may then be installed within the appropriate groove 182a, 182b in the block halves 180a, 180b and may function to maintain the halves together during operation. This configuration eliminates the need to provide a "flexible" internal carriage block with indents 176a, 176b, and may provide a carriage block that is easier to machine and assemble.

Figure 6:
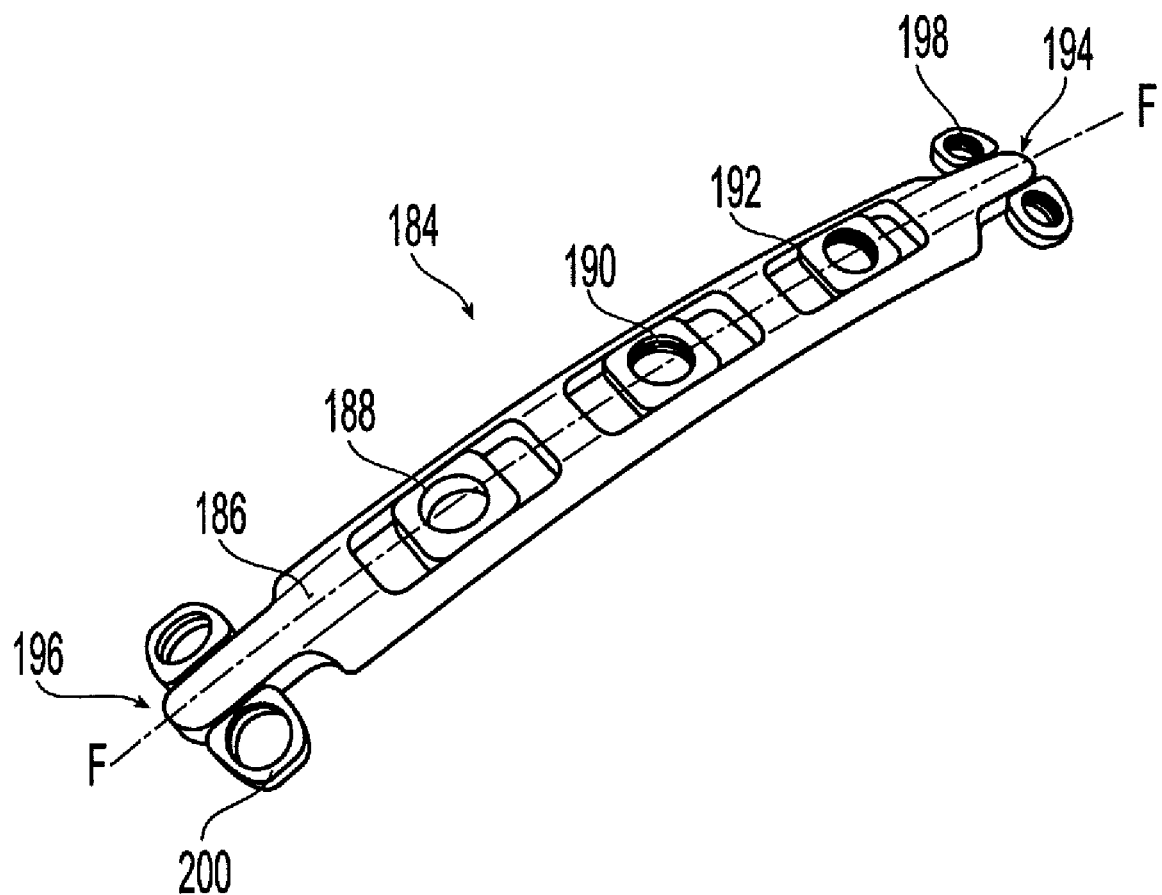
FIG. 6 is perspective view of another embodiment of a translational spinal plate with a plurality of internal carriage blocks.

The plate 184 of FIG. 6 may be used in a four-level fusion procedure and may have a plate portion 186, first, second and third internal carriage blocks 188, 190, 192 and first and second ends 194, 196 for engaging a pair of end carriage blocks 198, 200 in a manner similar to that described in relation to the plate of FIG. 5a. The plate portion 186 may have a longitudinal axis F-F, and may have first, second and third intermediate recesses 202, 204, 206 disposed along the axis F-F for cooperating with the first, second and third internal carriage blocks 188, 190, 192, respectively. It is noted that while the plate 184 is shown for use in a four-level fusion procedure, it could easily be configured for use in a three or two-level procedure simply by shortening the plate and providing fewer internal carriage blocks. Likewise, the plate portion 186 could be provided with one or more sets of holes, preferably slotted holes, in lieu of one or more of the internal carriage blocks.

In addition, the internal carriage blocks 188, 190, 192 may have any or all of the features described in relation to the plate 128 of FIG. 5a, and the end carriage blocks 198, 200 may have any or all of the features described in relation to FIGS. 1a-5c.

Figure 7A:
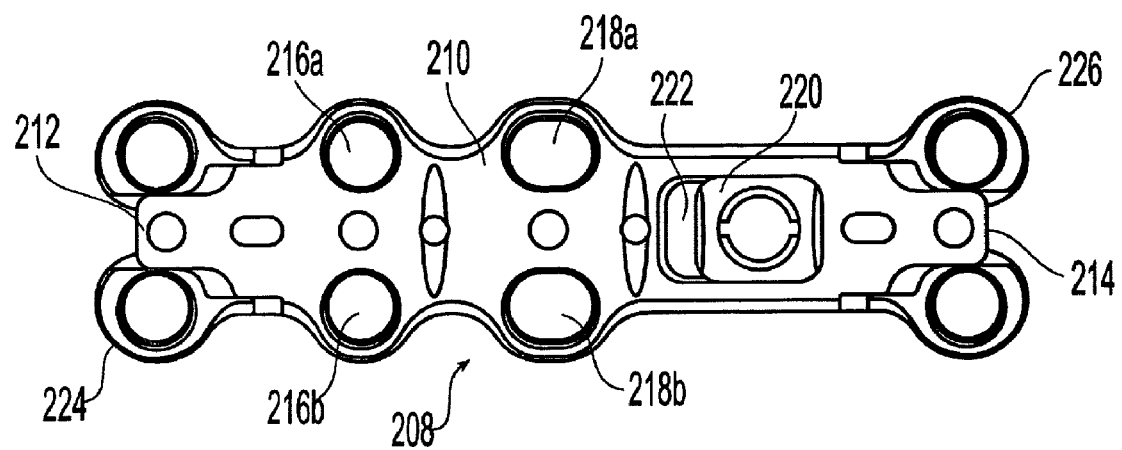
FIG. 7a is a top view of another embodiment of a translational spinal plate with both a pair of slotted bone screw holes and an internal carriage block.

The plate 208 of FIG. 7a combines some of the features of the previously described plates into a single plate for use in a four-level spinal fusion procedure. The plate 208 may have a fixed plate portion 210 with first and second ends 212, 214, one pair of round holes 216a, 216b for engaging a first vertebra, one pair of slotted holes 218a, 218b for engaging a second vertebra, one internal carriage block 220 disposed in recess 222 for engaging a third vertebra, and a pair of end carriage blocks 224, 226, each configured to engage a respective end 212, 214 of the fixed plate portion 210. Thus configured, the plate 208 may be rigidly fixed to the first vertebra, while the remaining vertebrae may translate with respect to the first vertebra via the slotted holes 218a, 218b, internal carriage block 220, and end carriage blocks 224, 226 as previously described. Moreover, all of the bone fastener holes may be configured similarly to that described in relation to FIGS. 1c and/or 4a-4b, and may have retaining clips 38 configured to retain a bone screw 44 therein.

Figure 7B:
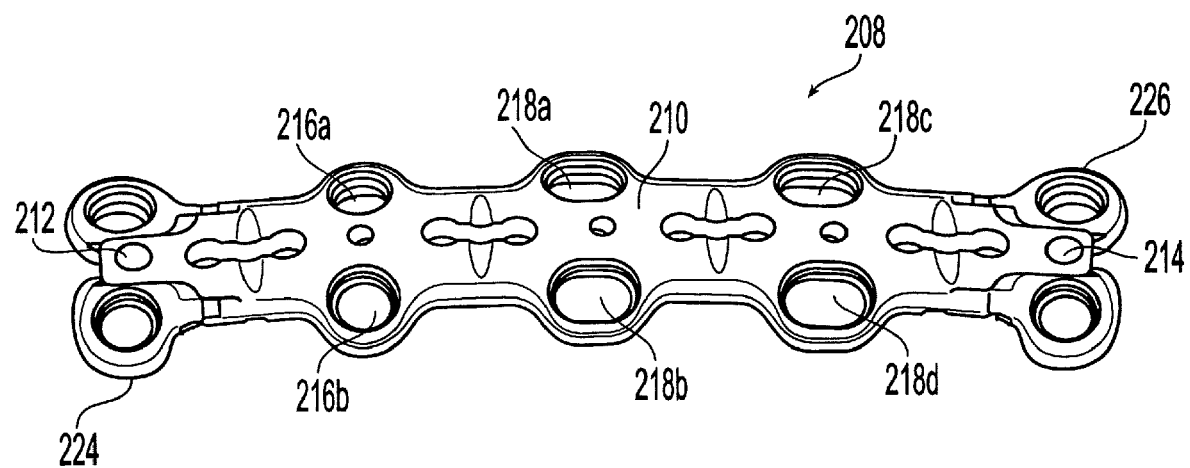
FIG. 7b is perspective view of another embodiment of a four-level translational spinal plate with two pairs of slotted holes.
Figure 7C:
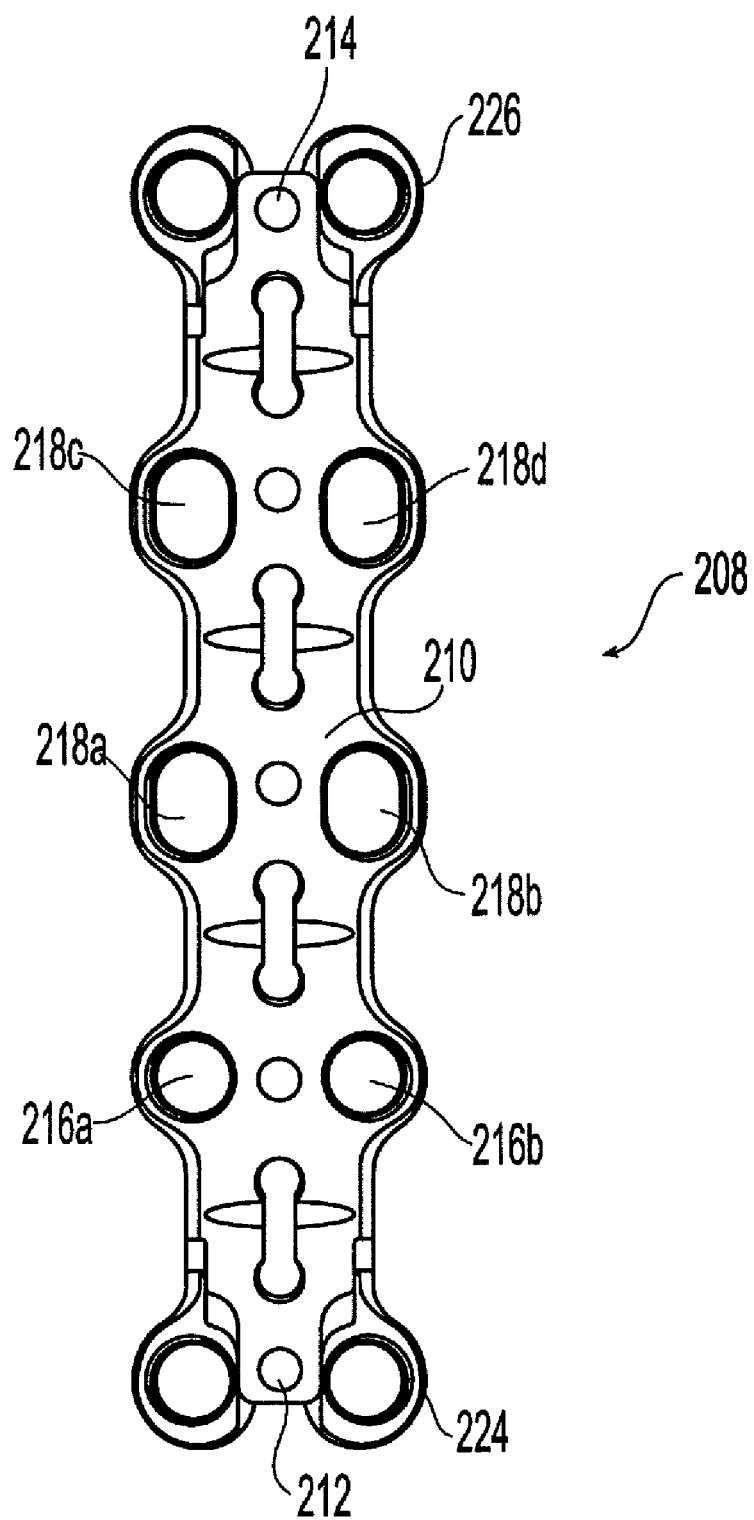
FIG. 7c is a top view of the plate of FIG. 7b.

FIGS. 7b-7c show a similar single plate for use in a four-level spinal fusion procedure, but without an internal carriage block 220. Instead, the embodiments of FIGS. 7b-7c have two pairs of slotted holes 218a, 218b and 218c, 218d.

Figure 8A:
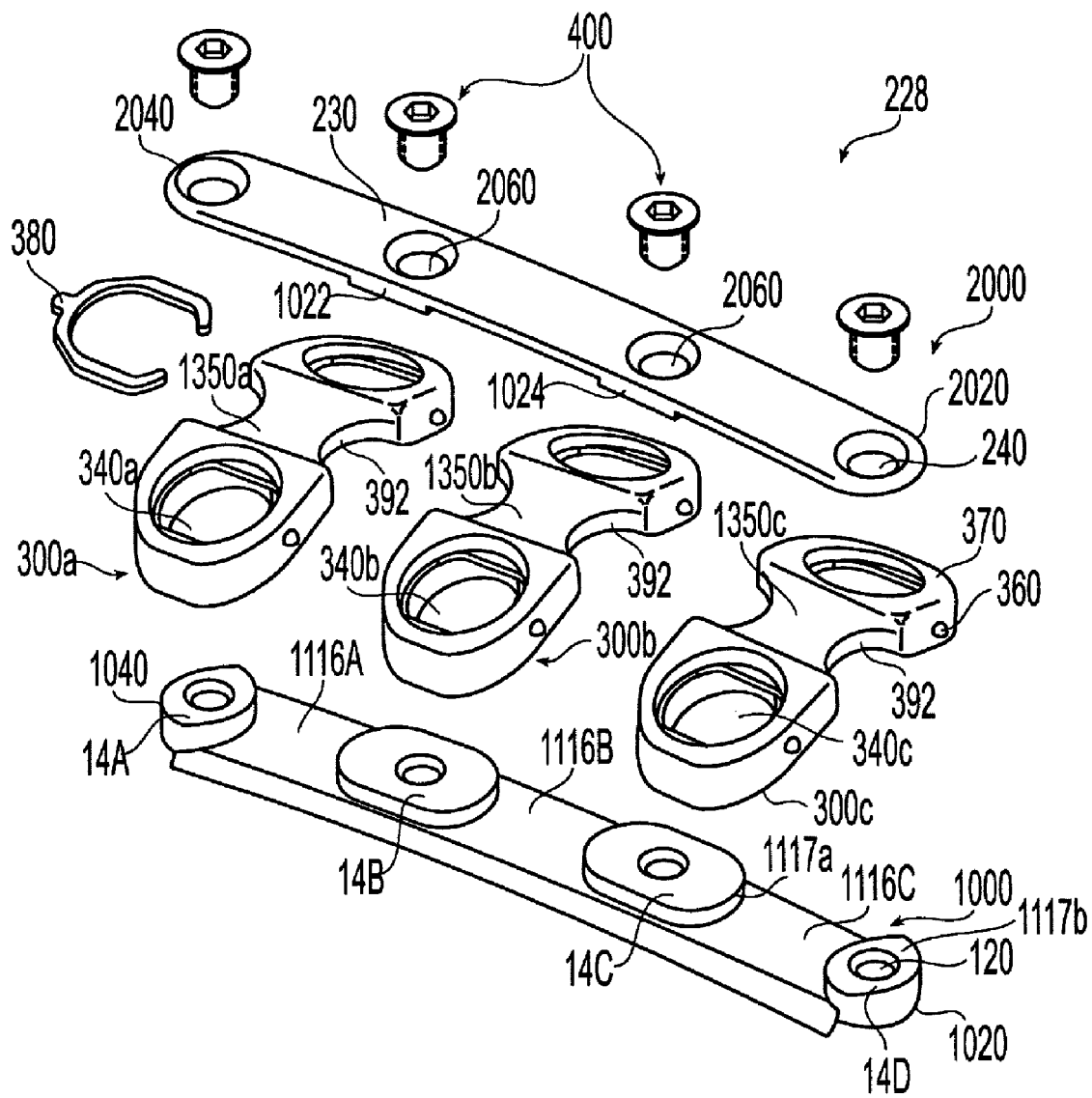
FIG. 8a is an exploded view of another embodiment of a translational spinal plate with a two-piece track-plate construction.

FIG. 8a shows a plate 228 for use in a two-level fusion procedure, the plate having a two-piece sandwich style plate portion 230 comprising a track base 1000 and top plate 2000. The plate portion 230 engages three carriage blocks 300a, 300b, 300c via respective recesses 1116a, 1116b, 1116c formed in the track base 1000.

The carriage blocks 300a, 300b, 300c each may include one or more fastener holes 340a, 340b, 340c configured to receive fasteners 44 to fix the carriage blocks to associated vertebrae. The track base 1000 may have first and second ends 1020, 1040 and may have a curved profile to allow the plate 228 to more closely match the contour of the patient's spine. The top plate 2000 may likewise have first and second ends 2020, 2040 and may have a curved profile that substantially matches that of the track base.

The top plate 2000 may have a pair of lateral alignment flanges 1022, 1024 and at least one bore 2060 for receiving a holding fastener 400 for securing the top plate 2000 to the track base 1000. Any appropriate fastening means may be provided to fix the top plate to the track base, including but not limited to screws, rivets, press-fit, laser welding, brazing, or suitable adhesives. The alignment flanges 1022, 1024 may serve to align the top plate and track base, and to provide the plate 228 with increased strength in bending and torsion.

The top plate 2000 and track base 1000 may be assembled so as to retain the carriage blocks 300a, 300b, 300c within associated recesses 1116a, 1116b, 1116c so that the carriage blocks may slide within the recesses, thus providing the desired translation capability between the engaged vertebrae. The carriage blocks engage the respective recesses via reduced-size central portions 1350a, 1350b, 1350c.

Figure 8B:
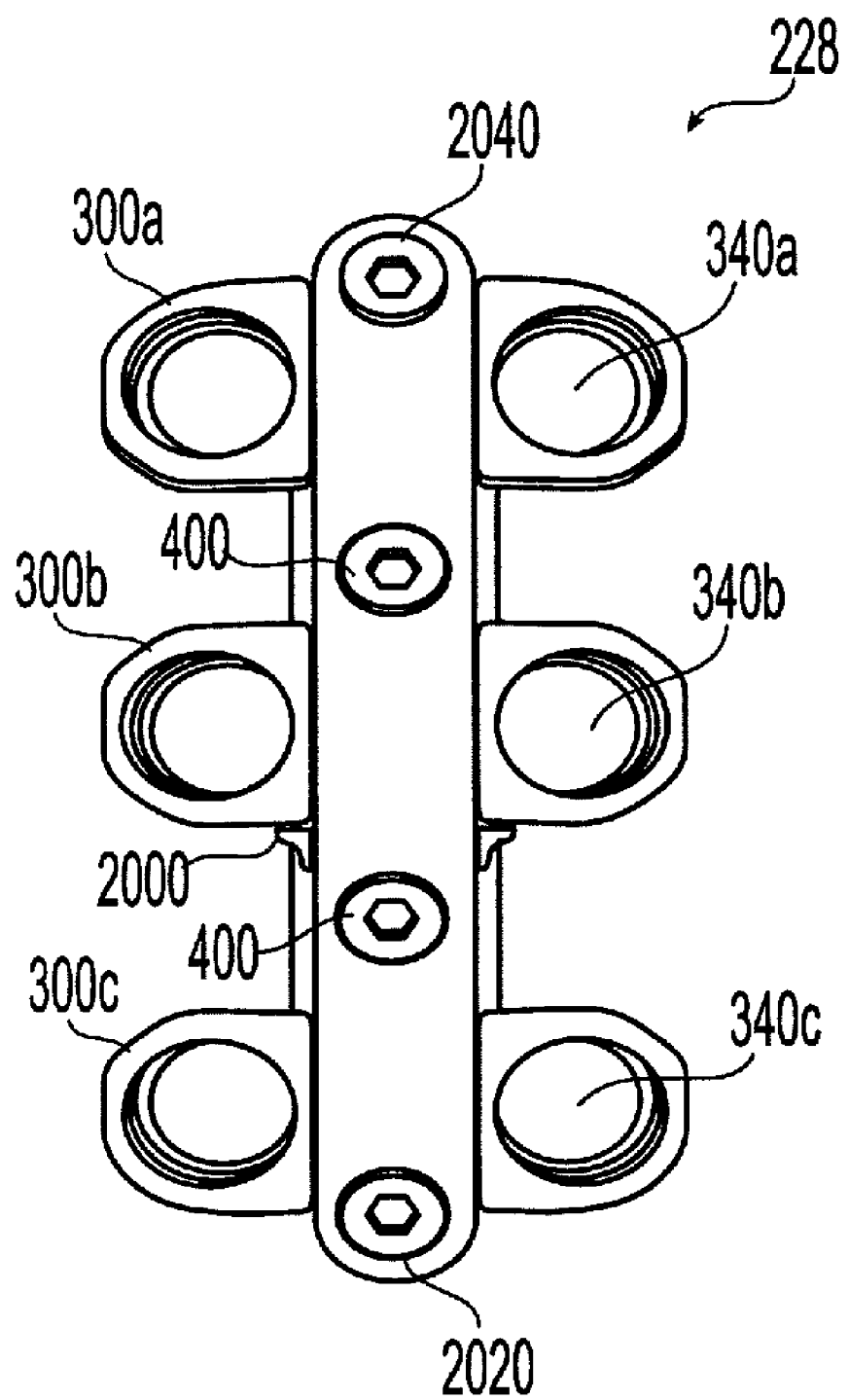
FIG. 8b is a top view of the plate of FIG. 8a in an assembled condition.

Two-hole carriage blocks 300a, 300b, 300c may be provided, and as previously described in relation to the plate of FIG. 1a, the carriage block fastener holes 340a, 340b, 340c, may be configured to receive retention clips 38 (see FIG. 2b) for retaining the bone fasteners 44 (see FIG. 2a) in the holes during operation. FIG. 8b shows the plate of FIG. 8a in the assembled position.

Figure 8C:
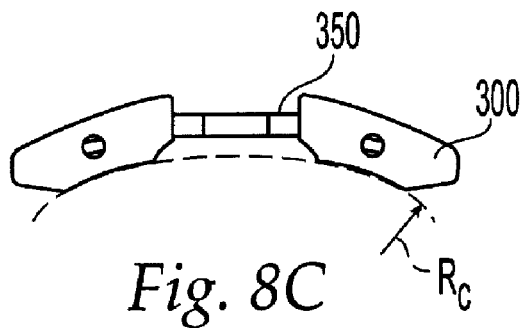
FIG. 8c is a front view of an embodiment of a symmetrical carriage block.
Figure 8D:
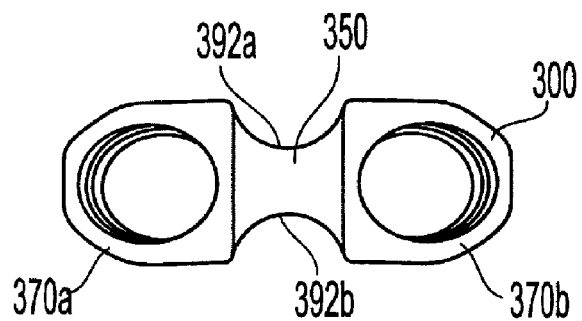
FIG. 8d is a top view of the carriage block of FIG. 8c.

FIGS. 8c-8f show carriage block 300 in greater detail. As illustrated in FIGS. 8c and 8d, carriage block 300 may comprise a pair of fastening portions 370a, 370b and a connecting portion 350 disposed therebetween. The connecting portion 350 may have first and second ends 392a, 392b, which may be configured to conform to corresponding outside and inside walls 1117a, 1117b of an associated plate recess 1116a, 1116b, 1116c into which the carriage block 300 will fit. In the illustrated embodiment, connection portion 350 has a concave first end 392a to engage a correspondingly curved recess end (outside wall 1117a or inside wall 1117b, see FIG. 8a).

Figure 8E:
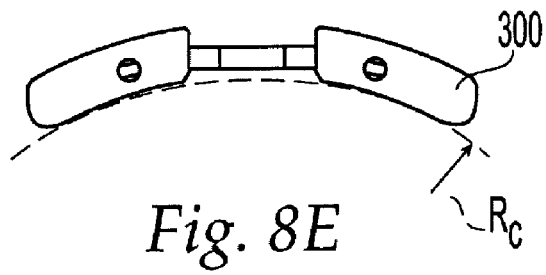
FIG. 8e is a front view of an embodiment of an offset carriage block.
Figure 8F:
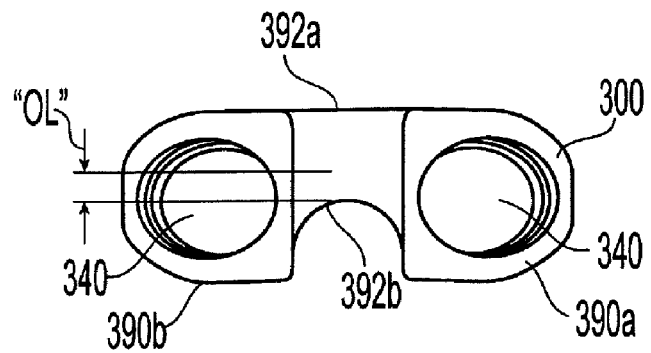
FIG. 8f is a top view of the carriage block of FIG. 8e.
Figure 8G:
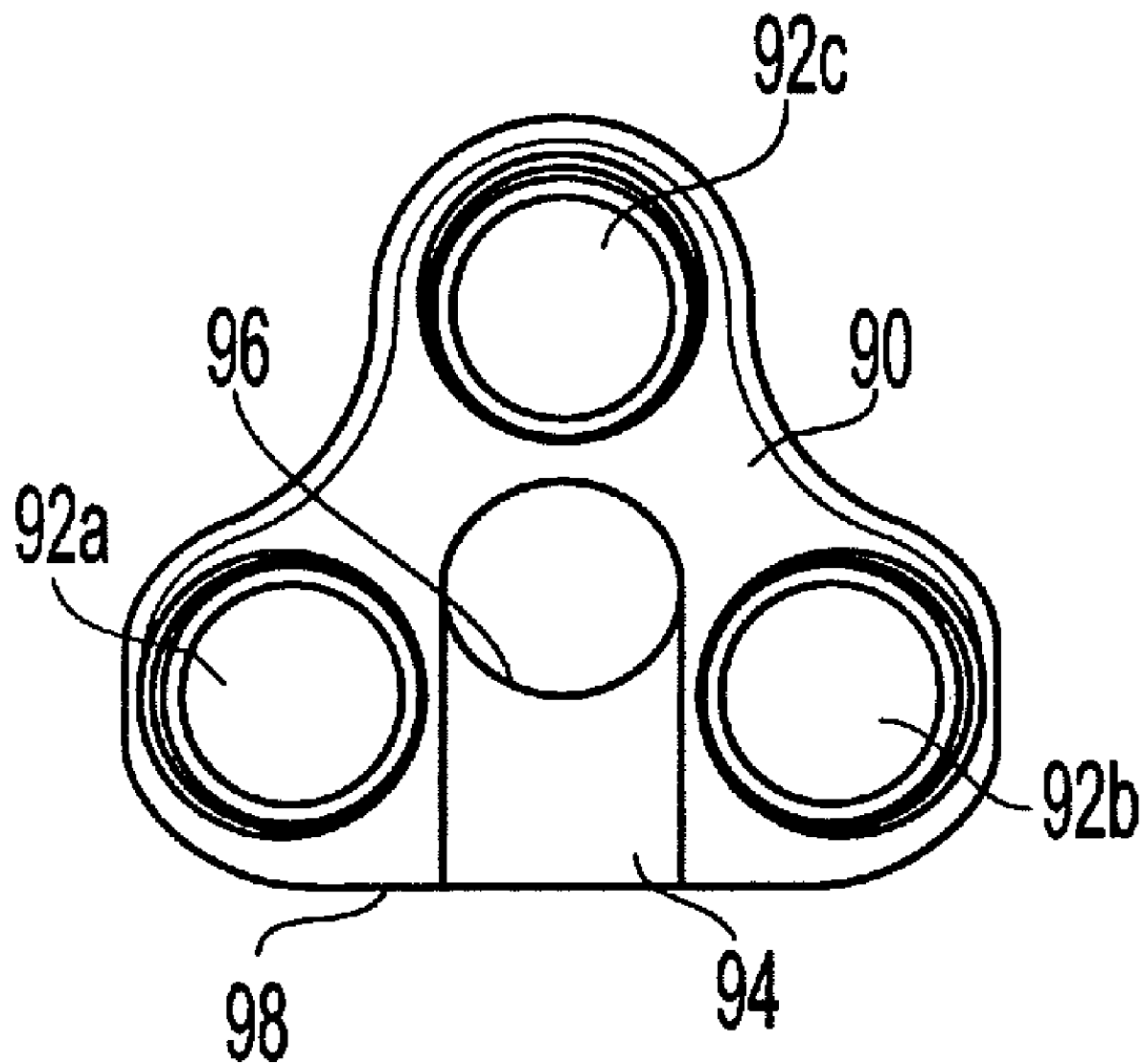

The carriage block 300 of FIGS. 8e and 8f have fastener holes 340 that may be offset longitudinally from the center of the connecting portion 35 by a length OL. This offset ensures that in use, the outer edges 390a, 390b of the carriage block 30 will not extend beyond the ends 2020, 2040 of the top plate 2000, even where the plate and carriage blocks are in the fully compressed configuration. Such an arrangement provides the advantage that it prevents any portion of the top plate 2000 from protruding either into or undesirably close to the adjacent disc space when the carriage blocks translate fully within their associated recesses.

The carriage block 300 may have compression and extension surfaces 392a, 392b configured to engage corresponding surfaces 1117a, 1117b of the associated recess 1116 formed in track base 1000. Thus configured, the connecting portions 350 of the carriage blocks 300a, 300b, 300c may be received within the corresponding recesses 1116a, 1116b, 1116c in the track base 1000 and may translate along the plate to provide the desired translation of adjacent vertebral bodies.

FIG. 8g shows an alternative carriage block 90 having three fastener holes 92a, 92b, 92c, that may be used with a plate such as the plate 61 shown in FIG. 3a. Fastener hole 92c may be offset from fastener holes 92a, 92b and may be disposed substantially along the longitudinal axis B-B of the plate 61. The additional fastener hole 92c may increase the retention of the plate with the associated vertebral body. This may be particularly advantageous where the plate is subjected to significant forces and moments in use which may tend to pull the fastener out of engagement with the bone.

The plate engaging portion 94 of the three-hole carriage block 90 may be slidably received within a plate, such as the carriage block-engaging portions 70, 72 of the plate 61 as previously described in relation to carriage blocks 74, 76. The plate engaging portion 94 may also comprise extension and compression stop surfaces 96, 98 similar to those described in relation to blocks 74, 76 to limit the total movement of the carriage block 90 along axis B-B with respect to the fixed plate portion 61. The extension and compression ranges of movement and resistance to movement may be the same as for the previously described carriage blocks.

Figure 9:
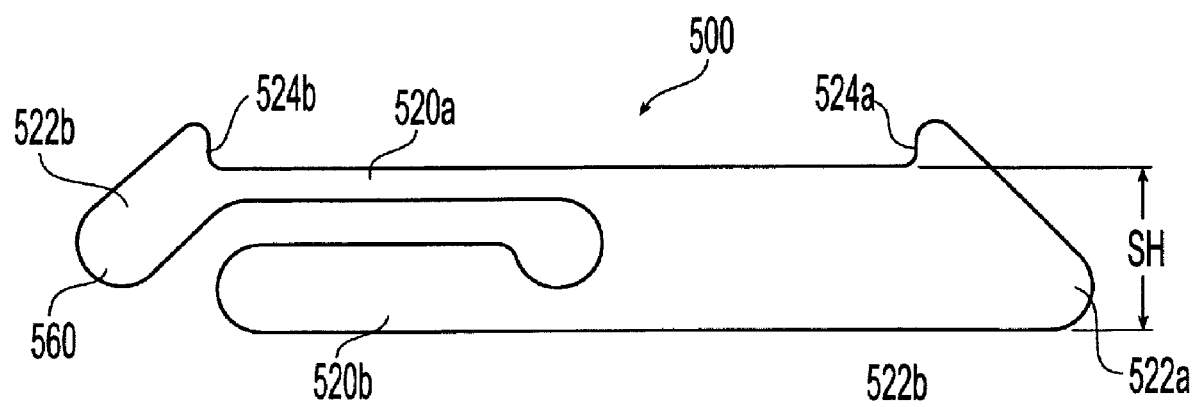
FIG. 9 is a top view of a motion-limiting shim.

In order provide the surgeon the option to limit or prevent pre- or post-implantation translation of any or all of the carriage blocks described herein (such as elements 4, 74, 76, and 300) for use with any plate or plate element described herein, a motion limiting shim 500, shown in FIG. 9, may be provided. Shim may be positioned between the carriage block 300 and one of the sides 1117a, 1117b of the associated recess 1116a, 1116b, 1116c. Such an arrangement may allow the surgeon to customize the amount and direction of translation of one or more of the carriage blocks. The shim 500 may be made of a flexible material, such as elgiloy or nitinol, or may be made of a suitable bioresorbable material. Shim 500 is preferably composed of a biocompatible material. As illustrated in FIG. 9, the shim 500 may have opposing flexible tabs 520a, 520b that may allow an operator to compress the shim to position it within the targeted recess 1116. In particular, flexible tab 520a may be actuated by applying pressure to bulbous tab 560. Shim 500 may have a height "SH" that may be the maximum distance a shim may occupy along the longitudinal axis of a plate. Moreover, shim 500 may have gripping tabs 522a, 522b that may allow an surgeon to grip the shim 500 to move it to a desired location within a plate, or remove it completely from a plate. Side surfaces 524a, 524b may correspond to the outer edges of a flange 1022 (see infra FIG. 10), or may generally correspond to a translating surface of a carriage block and/or plate segment, depending at least in part how shim 500 is situated in relation to a carriage block and/or plate segment.

Figure 10:
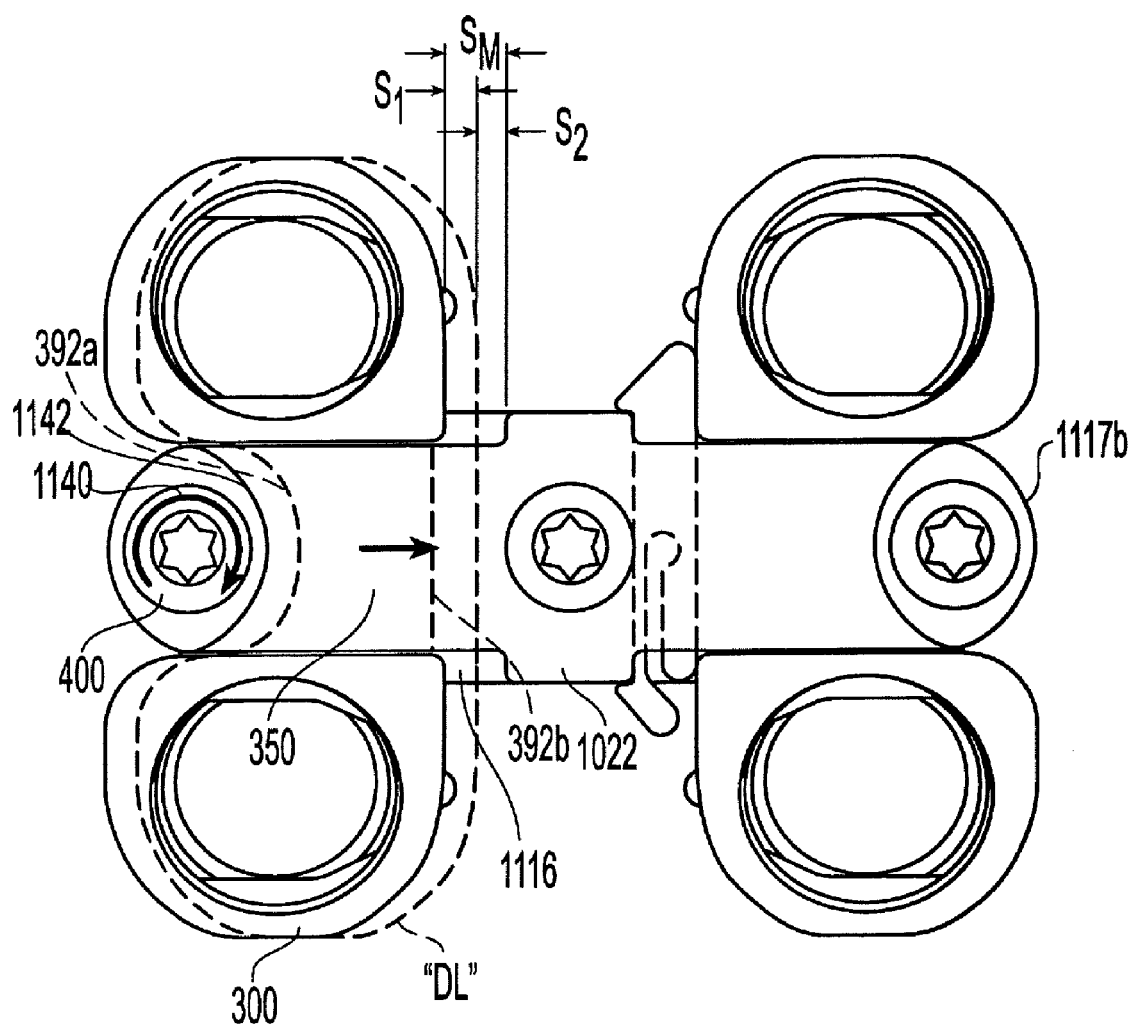
FIG. 10 is a top view of another embodiment of a translational spinal plate, this embodiment having a cam-compression feature.

FIG. 10 illustrates a plate having a cam-compression feature for use with any of the previously described plates. This feature is operable to allow the surgeon to adjust the recess length to minimize or prevent translation of the associated carriage block, or to induce a compression force between adjacent vertebrae to aid in seating a spinal fusion implant inserted therebetween.

The cam 1140 may be elliptical, with an arcuate camming surface 1142 configured to correspond to an arcuate surface 392 on the connecting portion 350 of the associated carriage block 300 (see, e.g., FIG. 8c). The cam 1140 may have an unactuated position in which the cam major diameter is oriented substantially perpendicular to the longitudinal axis of the plate, and an actuated position in which the cam major diameter is oriented substantially parallel with respect to the longitudinal axis of the plate. The unactuated cam position may correspond to a maximum recess length $S_M$, while the actuated position may correspond to a minimum recess length S2.

Thus, prior to fixing the carriage blocks to the adjacent vertebrae, the cam 1140 may be rotated sufficiently to shift the adjacent carriage block 300 in a first direction toward the one of the walls 1117b of the recess 1116, thus minimizing or eliminating the gap between the inside wall and the connecting portion 350 of the carriage block 300. Once the cam 1140 position is set, the carriage blocks 300 may then be fixed to the adjacent vertebrae to provide a translation plate having, if desired, a reduced translation length for each carriage block 300. This provides the benefit of allowing the surgeon to easily adjust the amount of translation desired for each level of fixation to suit the anatomy and physiology of the individual patient.

The cam 1140 may also be used to induce a compression force between adjacent vertebrae to aid in seating a spinal fusion implant inserted therebetween. Thus, first and second carriage blocks 300a, 300b may be fixed to adjacent vertebrae with the cam 1140 in the unactuated position. Thereafter, the cam 1140 may be rotated to the actuated position, which may shift the first carriage block 300a toward the second carriage block 300b. This movement may cause the underlying vertebra to move with the first carriage block 300a toward the second carriage block 300b, thus reducing the space between the vertebrae and applying a compressive force between the vertebral end plates and a spinal fusion spacer placed therebetween.

As can be seen in FIG. 10, dashed line "DL" shows the expected position of the carriage block 300 after a single 90-degree rotation of the cam 1140. To achieve this expected position, carriage block 300 would move a longitudinal distance S1 toward the center flange 1022. Further rotation of the cam 140 would move the carriage block 30 a second distance S2, until the second end 390B of the carriage block 300 abuts the center flange 1022 of the top plate 20.

The cam 1140 may be secured to the track base 1000 with a holding fastener 400 or any other appropriate fastening method. In one embodiment, the fastener may serve both to secure the cam 1140 to the track base 1000 and to provide a means of actuating the cam. Thus, the fastener 400 may have a recess suitable for receiving a driving and/or adjusting tool.

Figure 11:
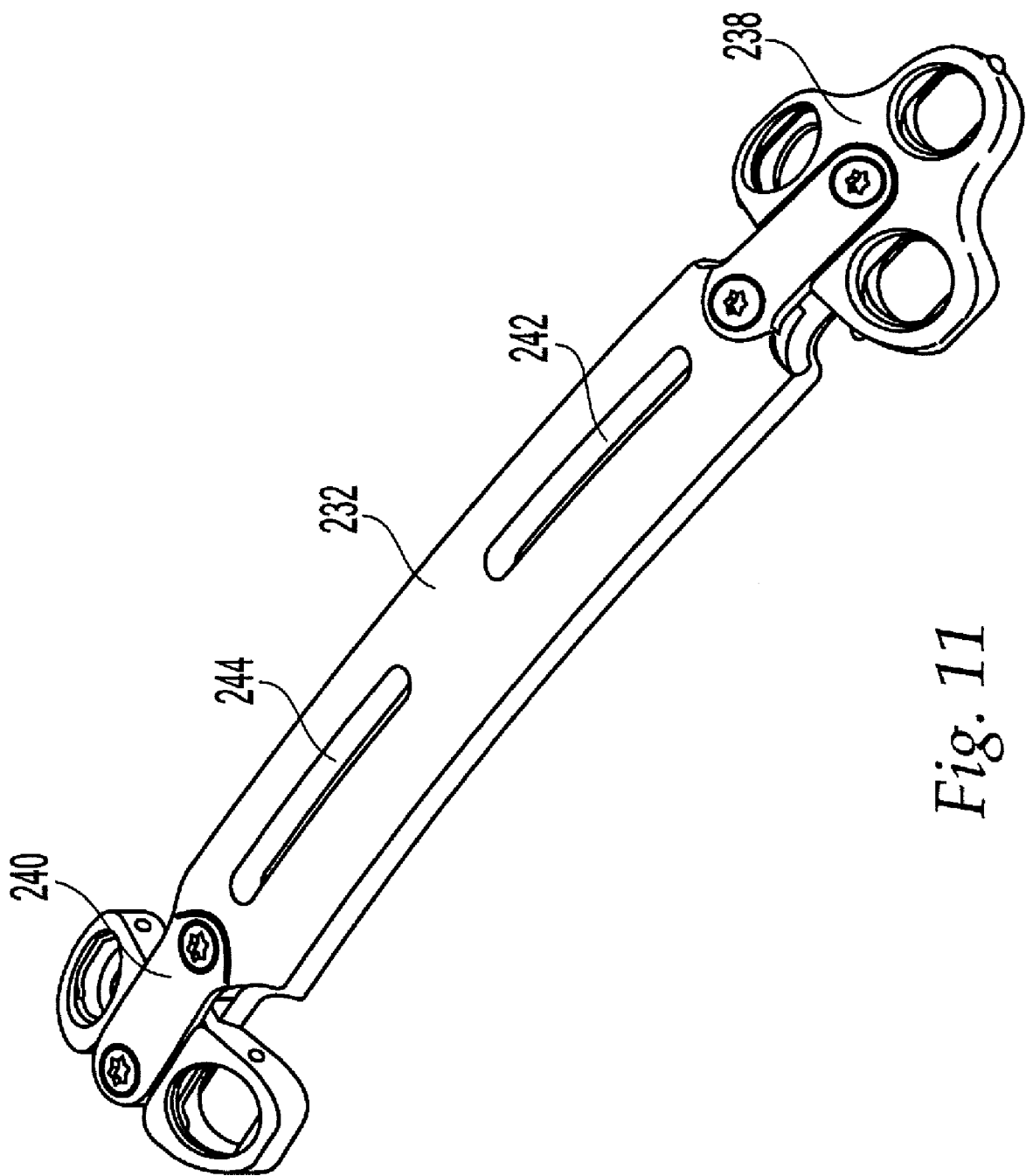
FIG. 11 is a perspective view of a corpectomy model of a translational spinal plate.

FIG. 11 shows a plate 232 for use in a corpectomy procedure, in which at least a portion of at least one vertebral element is removed. Thus, the plate 232 spans the space left by the removed element or elements. Plate 232 may have a plate portion 234 with first and second ends 236 configured to cooperate with a pair of end carriage blocks 238, 240. In the illustrated embodiment, end carriage block 238 has a third plate hole as previously described in relation to FIG. 8g. Plate 232 further comprises a pair of elongated viewing windows 242, 244 suitable to allow the surgeon to visualize a corpectomy graft placed between the affected vertebrae. The plate 232 of FIG. 11 may further incorporate any or all of the features previously described in relation to the embodiments of FIGS. 1a-10 (e.g., plate and carriage block curvatures, straight and offset carriage blocks, shim arrangements, cam features, fastener locking clips, etc.)

Figure 12B:
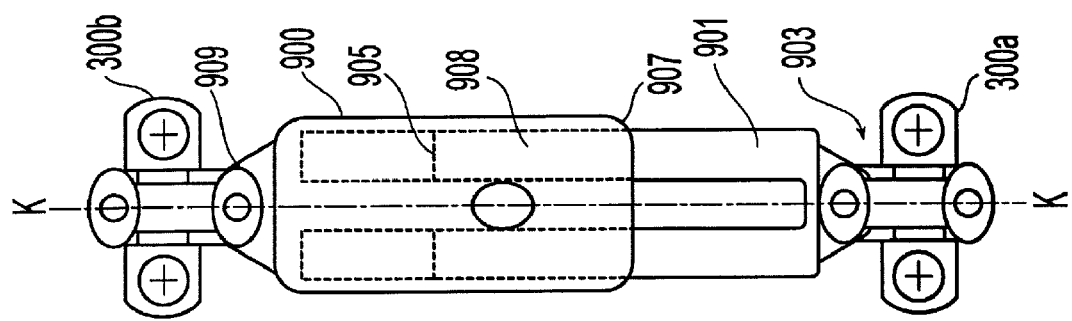
FIG. 12b is a top view of the plate of FIG. 12a in an extended position.
Figure 12A:
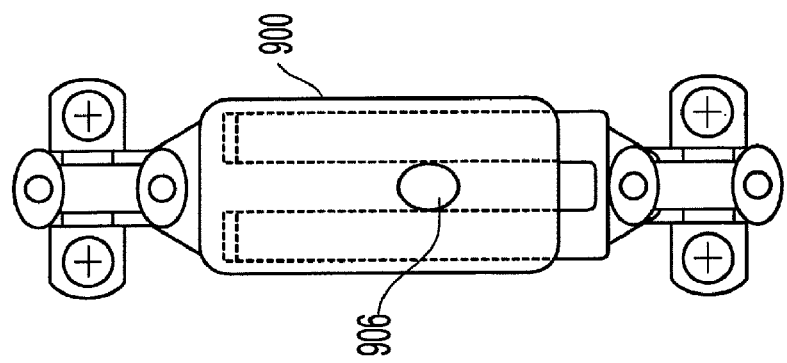
FIG. 12a is a top view of a further embodiment of an extensible translational spinal plate in a compressed position.

FIGS. 12a and 12b show a plate 900 that may be provided in two extensible pieces 901, 908, which may allow the plate itself to bear a portion of the translation. This extensible two-piece design also may allow the surgeon to adjust the length of the plate to fit the anatomy of a particular patient. Thus first extensible piece 901 may have a first end 903 engaged to a first carriage block assembly 300a, and a second end 905 configured to be telescopically received within a first end 907 of the second extensible piece 908. Likewise, the second extensible piece 908 may have a first end 907 configured for telescopic engagement with the first piece 901 and a second end 909 engaged to a second carriage block assembly 300b. The second extensible piece 908 may have a locking device 906, which may lock the relative positions of the first and second pieces. In the illustrated embodiment, the locking device 906 is an elliptical cam associated with both the first and second plate portions 901, 908. The cam 906 may have a major diameter substantially aligned with the longitudinal axis K-K of the plate 900 when in the unlocked position, such that rotating the cam 906 slightly may configure it to the locked position, thereby fixing the pieces 901, 908 together. After adjustment of first extension piece 901 and second extension piece 908, the pieces may be fixed together so that they will not move relative to each other upon implantation in the spine. Thus, it is intended that upon implantation, first extension piece 901 will not move relative to second extension piece 908 in situ. Meanwhile, carriage blocks 300a, 300b would provide for in situ movement relative to the first and second extension pieces 901, 908, and to each other. upon implantation of the plate 900. FIG. 12a shows plate 900 in a closed or compressed position, while FIG. 12b shows the plate 900 in an open or extended position. As with the previous embodiments, the plate of this embodiment may comprise any or all of the applicable plate and carriage block features described in relation to all previous embodiments. Further, the plate of this embodiment may be used for single or multiple-level corpectomy or fusion procedures or combinations thereof.

Figure 13A:
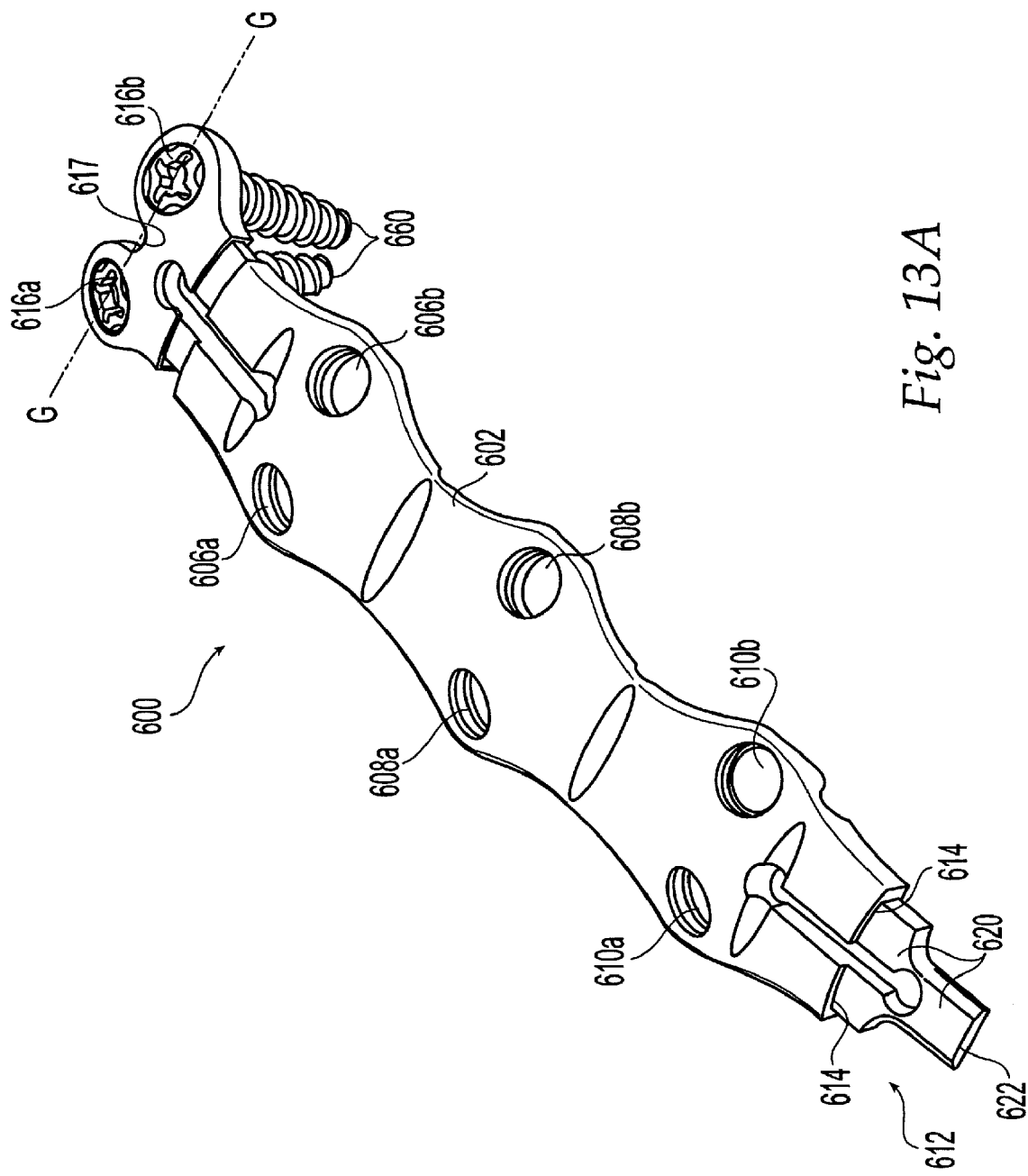
FIG. 13a is a perspective view of another embodiment of a translational spinal plate having a dovetail design.
Figure 13B:
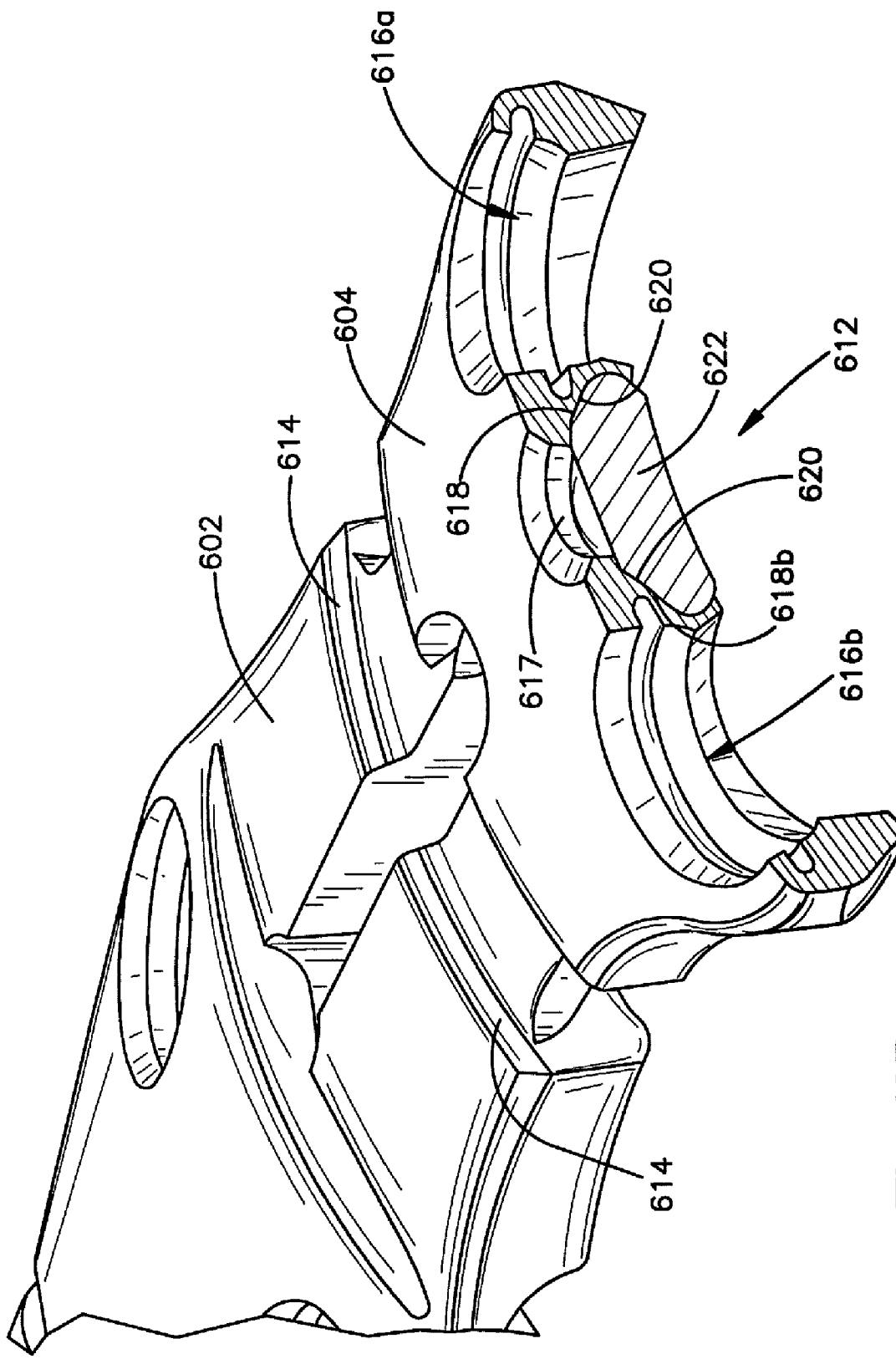
FIG. 13b is a cross-sectional view of the plate of FIG. 13a taken along the line G-G.

FIGS. 13a and 13b show another embodiment of a fixation assembly 600 including a plate 602 with dovetail portions 612 configured to receive at least a portion of a carriage block 604. In this embodiment, carriage block 604 is allowed to initially engage a dovetail portion 612, and thereafter the end 622 of the dovetail portion 612 is deformed at or near the end 617 of the carriage block 604 to effectively limit the motion of the carriage block and prevent it from disengaging with the plate 602. End 622 may be deformed by any suitable method, including swaging.

Plate 602 may have fastener holes 606a, 606b, 608a, 608b, 610a, 610b, which may be circular or slot-shaped. Moreover, plate 602 may include any or all of the characteristics of previously described plates, including clips, recesses, internal carriage blocks, etc.

Carriage block 604 may translate along dovetail portion 612 in use, which may be limited by the deformed end 622 in one direction, and a stop surface 614 in another direction. As described in more detail above, carriage block 604 may translate in situ, with or without fasteners 660 inserted into fastener hole 616a, 616b, which may provide locations for inserting fasteners 660 into a bone segment.

As shown in detail in FIG. 13b, carriage block 604 may have translation surfaces 618, and plate 602 may have translation surfaces 620. As described in more detail above, as carriage block 604 translates with respect to plate 602, translation surfaces 618, 620 may slidingly engage, and may create a variable amount of friction along the length of the dovetail portion 612. As with plate 602, carriage block 604 may include any or all of the characteristics of carriage blocks described above.

Dovetail portion 612 may have a variety of shapes and sizes, based in part on the desired strength of the assembly 600. For instance, it may be beneficial to have a wider, and overall larger, dovetail portion 612 where the expected in situ forces on the assembly 600 are expected to be substantial.

Figure 14A:
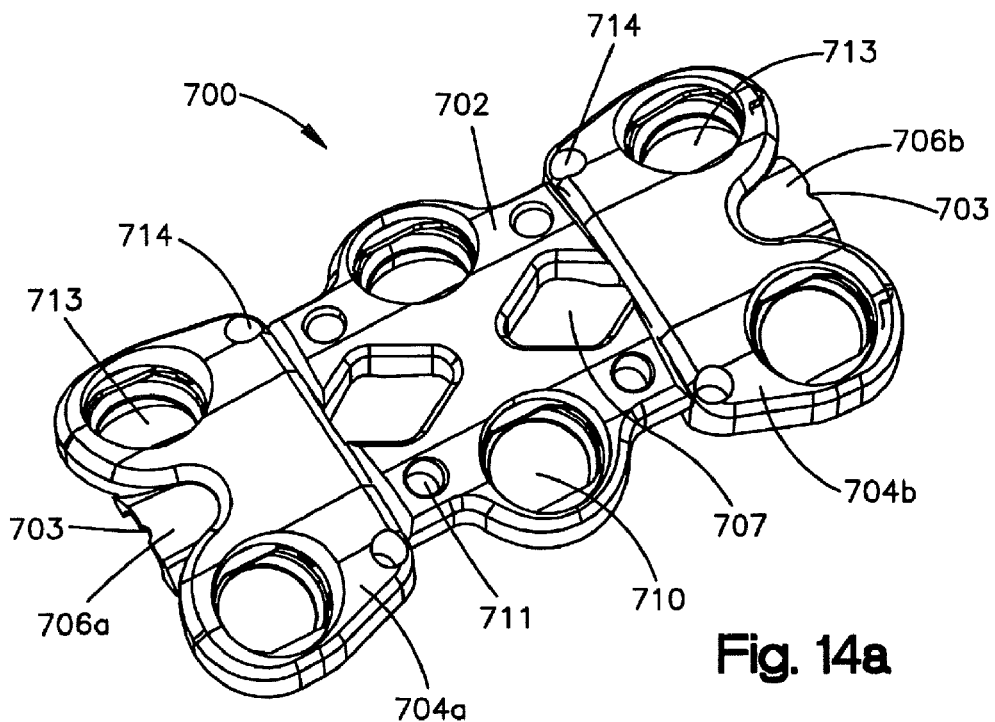
FIG. 14a is a perspective view of yet another embodiment of a translational spinal plate having a dovetail design in a compressed condition.
Figure 14B:
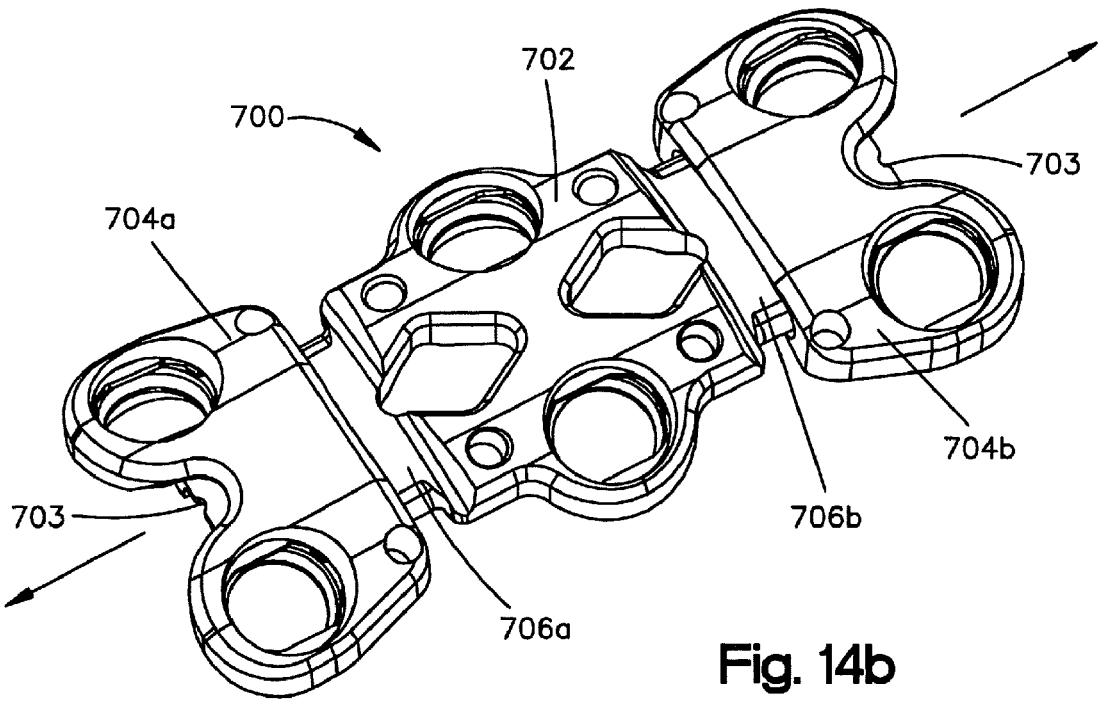
FIG. 14b is a perspective view of the plate of FIG. 14a in an expanded condition.

FIGS. 14*a*-14*b* are perspective views of yet another embodiment of a fixation assembly 700 having a plate 702 and carriage blocks 704*a*, 704*b*. Plate 702 may have a window 707 for increased visualization, and at least one fixation hole 710 with at least one drill guide key 711 disposed adjacent to the fixation hole 710. Similarly, carriage blocks 704*a*, 704*b* may also have fixation holes 713 and drill guide keys 714. Drill guide keys 711, 714 may receive at least a portion of a drill guide (not shown), and may assist in aligning a drill barrel (not shown) with a fixation hole.

In this embodiment, plate 702 has ends 703, and may engage carriage blocks 704*a*, 704*b* at tapered engaging surfaces 706*a*, 706*b*, respectively. Ends 703 of plate 702 may be shaped and/or formed such that carriage blocks 704*a*, 704*b* are prevented from sliding off the plate 702. As seen in FIG. 14*a*, carriage blocks 704*a*, 704*b* are in a compressed condition, whereby the assembly 700 may be in its shortest configuration along its longitudinal axis. FIG. 14*b* shows the assembly 700 in an expanded condition, whereby carriage blocks 704*a*, 704*b* each have translated along tapered engaging surfaces 706*a*, 706*b*, respectively, and in the direction of the adjacent arrows. In this configuration, the overall length of assembly 700 may be greater along the longitudinal axis, as compared to the configuration shown in FIG. 14*a*.

Figure 15:
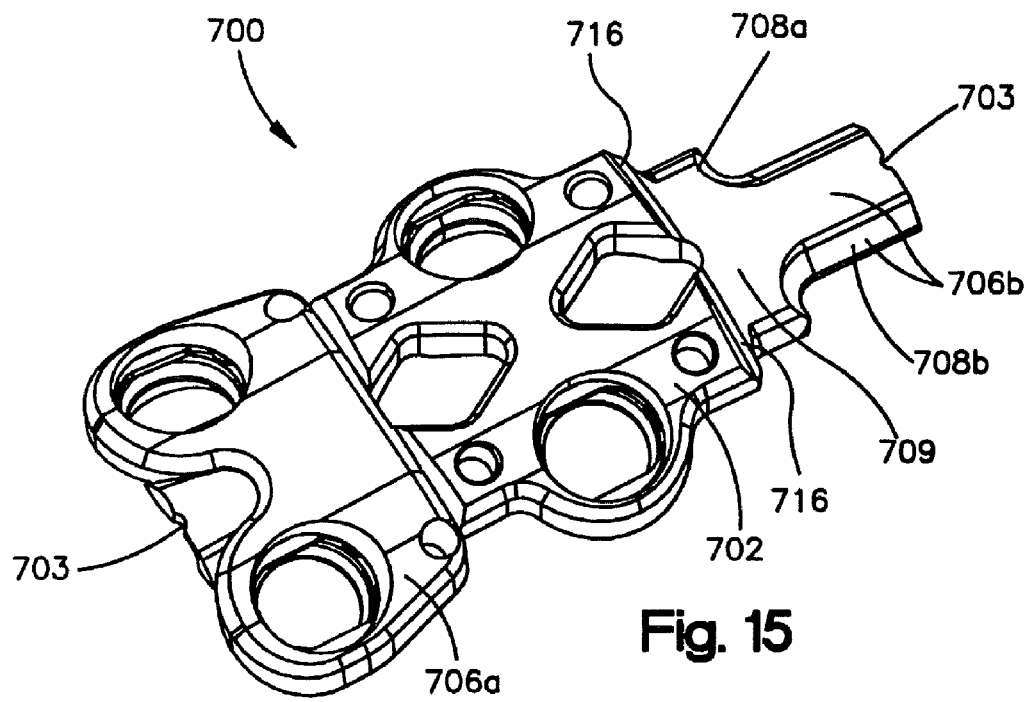
FIG. 15 is a perspective view of the base plate of FIGS. 14a-14b, with a carriage block removed for clarity.

The tapered engaging surface 706*b* is shown in more detail in FIG. 15. As seen in this embodiment, tapered engaging surface 706*b* has side tapered surfaces 708*a*, 708*b*, with a substantially flat surface 709 disposed therebetween. Side tapered surfaces 708*a*, 708*b* may be progressively tapered, such that the resistance between a carriage block 704*b* and the tapered engage surface 706*b* increases as the carriage block 704*b* (not shown, for clarity) attempts to translate toward the center of plate 702. The result of such an arrangement may be that it requires more force to compress assembly 700, than is required to lengthen assembly 700. As further seen in FIG. 15, plate 702 may also have stops 716, which may limit the movement of carriage block 704*b* relative to the plate 702.

Figure 16:
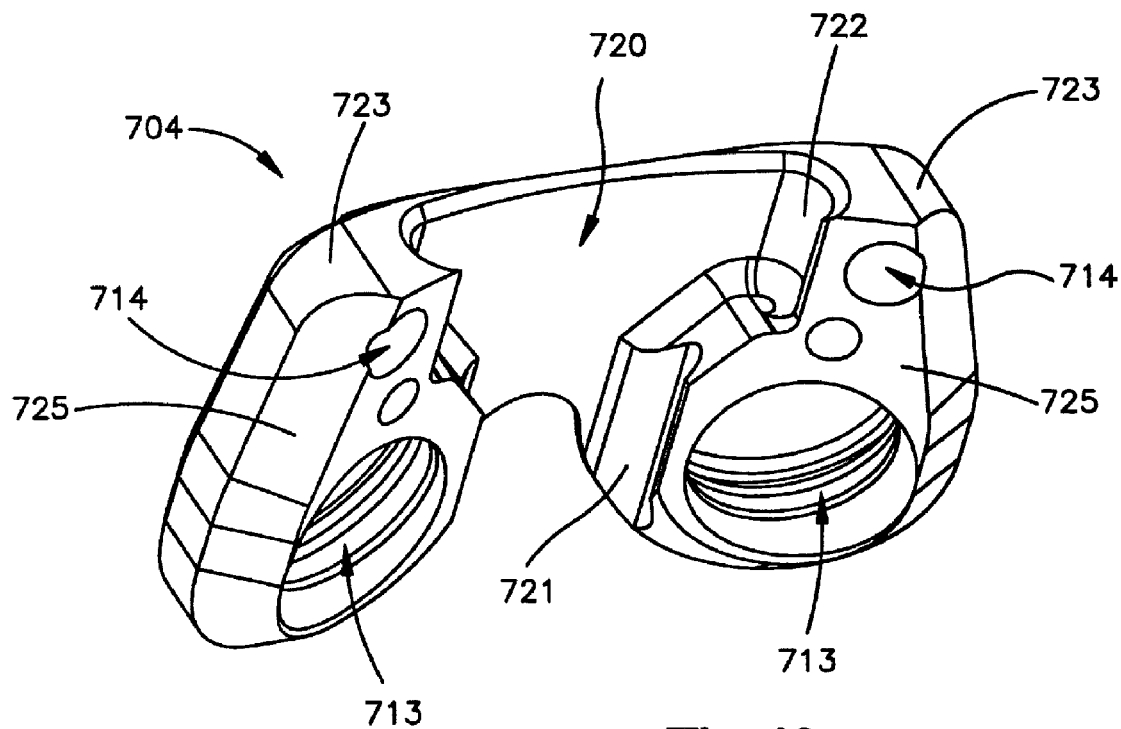
FIG. 16 is a perspective view of a carriage block for use with the plate of FIG. 15.

An embodiment of a carriage block 704 is shown in FIG. 16, wherein carriage block 704 may have fixation holes 713 and drill guide keys 714, as also shown in FIGS. 14*a*-15. As also seen in this embodiment, carriage block 704 may have a contoured opening 720 having tapered surfaces 721, 722 for engaging a tapered engaging surface 706 of plate 702, and disposed between lobes 725. Carriage block 704 may engage a tapered engaging surface 706 of plate 702 in such a way that as carriage block 704 is urged toward the center of plate 702 (i.e. toward a more compressed condition), carriage block 704 flexes such that lobes 725 are pushed upward by the tapered engaging surface 706 of plate 702. If the tapered engaging surface 706 is contoured to provide progressive resistance, the carriage block 704 may experience greater flexure as it is progressively urged closer to the center of plate 702. As such, carriage block 704 may be constructed of a resilient material which may flex back upon the movement of the carriage block 704 away from the center of the plate 702 and toward the end 703 of plate 702 (i.e. toward a more expanded condition).

Progressive resistance of a tapered engaging surface 706 may be achieved by increasing the angle of tapered side surfaces 708*a*, 708*b* along the longitudinal axis of plate 702. Progressive resistance may also be achieved by surface roughening. Other methods will be appreciated by those skilled in the art.

Figure 17A:
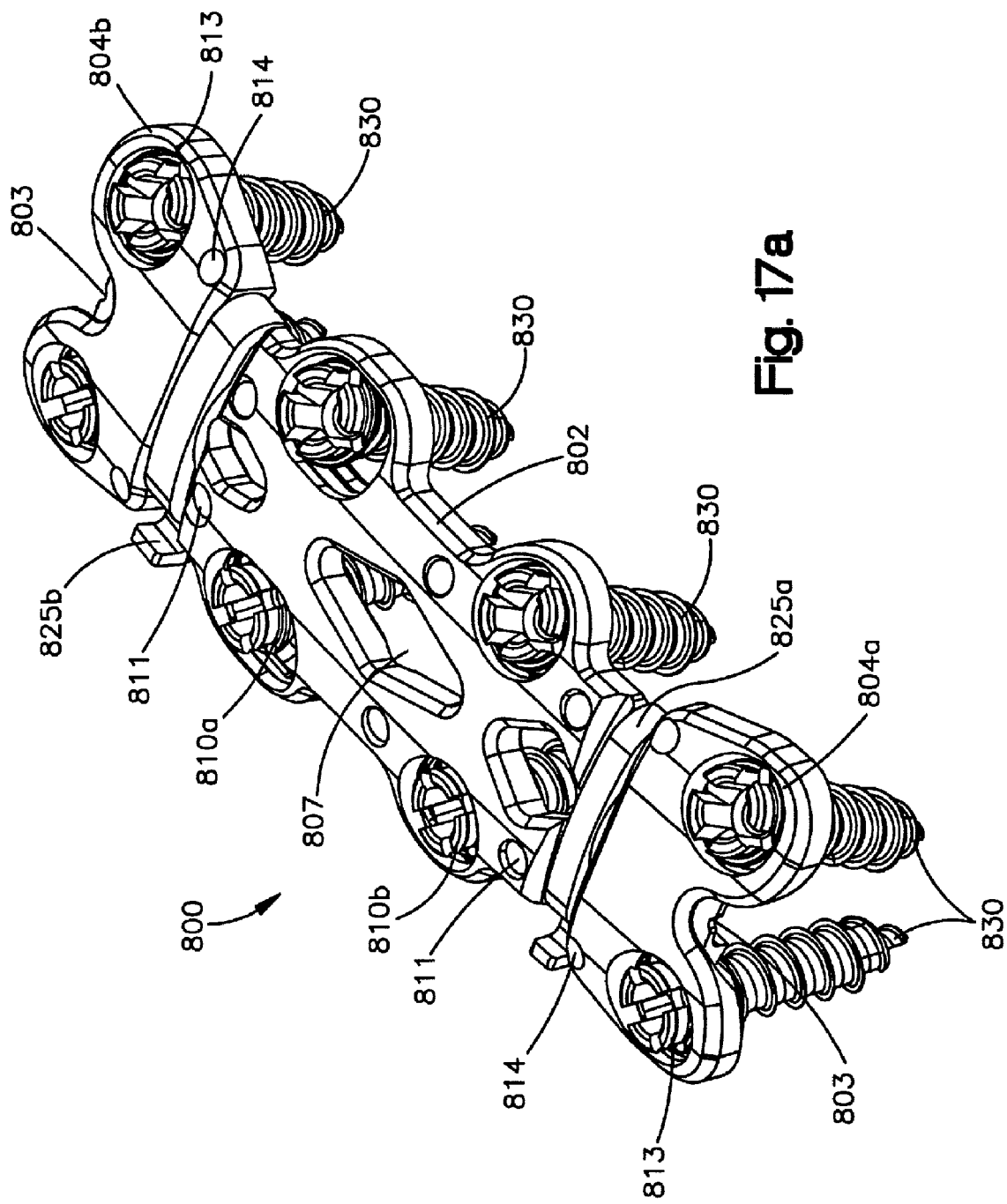
FIG. 17a is a perspective view of still another embodiment of a translational spinal plate having a dovetail design in a expanded condition.

Another embodiment of a fixation assembly 800 is shown in FIGS. 17*a*-17*b*. In this embodiment, plate 802 may have a plurality of windows 807, and two sets of fixation holes 810*a*, 810*b*, wherein fixation holes 810*a* may be substantially slot-shaped, and fixation holes 810*b* may be substantially circular. Fasteners 830 may be configured to translate within slot-shaped holes 810*a*. Plate 802 may also have ends 803, and tapered engaging surfaces 806 with carriage blocks 804*a*, 804*b* disposed thereon. Carriage blocks 804*a*, 804*b* may again have fixation holes 813 for receiving a fastener 830. Plate 802 and carriage blocks 804*a*, 804*b* may also each have drill guide keys 811, 814 for the same purposes as discussed above in relation to FIGS. 14*a*-14*b*. Fastener 830 may be a screw.

Assembly 800 may also initially have tabs 825*a*, 825*b* disposed between carriage blocks 804*a*, 804*b* and plate 802. In use, tabs 825*a*, 825*b* may serve to space carriage blocks 804*a*, 804*b* toward ends 803, which may configure assembly 800 in an expanded condition. This may be advantageous for implantation purposes, as it may be beneficial to install assembly 800 into a patient with the assembly 800 in an expanded condition. Tabs 825*a*, 825*b* are shown to be removed in FIG. 17*b*. In this embodiment, carriage block 804*b* has translated completed toward the center of the plate 802, in the direction of the adjacent arrow. In contrast, carriage block 804*a* has not translated, revealing a portion of the tapered engaging surface 806*a* and stops 816 of plate 802. As such, the embodiment of FIG. 17*b* is in a partially expanded (or partially compressed) condition. In use, a surgeon preferably will remove tabs 825*a*, 825*b* after implanting assembly 800 in a patient. Tabs 825*a*, 825*b* may be disposable.

It is expressly contemplated that progressive resistance may be utilized with all embodiments as shown herein, as will be appreciated by those of skill in the art. Moreover, it is contemplated that the components and features of one embodiment may be combined and/or substituted for similar components in another embodiment. Lastly, progressive resistance may be provided in any suitable direction and/or pattern. For instance, a tapered engaging surface 706, 806 may be tapered such that progressive resistance is provided as a carriage block 704, 804 translates toward the end 703, 803 of the plate 702, 802, instead of toward the center of the plate 702, 802.

It should be noted that the aforementioned descriptions and illustrations have been provided as examples of the configurations of translation plates that may be designed and assembled using the principles of the invention. These examples will be understood to one of ordinary skill in the art as being non-limiting in that a translating plate employing one or more of the disclosed features may be produced as desired or required for a particular patient's need. Thus, the features disclosed are "modular" in nature.

For example, the plate itself may be provided in either the one-piece design of FIGS. 1*a*-7*c*, or the two piece design having a top plate and track base of FIGS. 8*a*-8*b*. The one or two piece plate designs also may be provided with integral screw holes (FIGS. 1*a*-7*c*) to allow the plate element itself to be screwed to an underlying vertebra, or they may not have integral screws holes (FIGS. 8*a*-8*g* and 10-12*b*) such that the plate itself engages the underlying vertebrae only via the carriage blocks.

Furthermore, the one or two piece plates may employ any combination of carriage block designs desired (e.g. offset type (FIGS. 8e-8f), non-offset type (FIGS. 8c-8d), third-hole type (FIG. 8g) or internal type (FIGS. 5a-5c, 6, 7a)).

Each of the fasteners and fixation plates disclosed herein may be formed of a titanium alloy such as titanium-aluminum-niobium, which may be anodized. One material for use with each of the plates and screws described herein is Ti-6Al-7Nb, with a density of about 4.52 gm/cc, a modulus of elasticity of about 105 GPa, an ultimate tensile strength of about 900 MPa, and a yield strength of about 800 MPa. Surfaces of the fasteners may also be burr free, with all sharp edges having a radius to a maximum of about 0.1 mm. Further, the retention clips 38 may be fabricated from titanium, titanium alloy, or elgiloy.

While the invention has been shown and described herein with reference to particular embodiments, it is to be understood that the various additions, substitutions, or modifications of form, structure, arrangement, proportions, materials, and components and otherwise, used in the practice and which are particularly adapted to specific environments and operative requirements, may be made to the described embodiments without departing from the spirit and scope of the present invention. Accordingly, it should be understood that the embodiments disclosed herein are merely illustrative of the principles of the invention. Various other modifications may be made by those skilled in the art which will embody the principles of the invention and fall within the spirit and the scope thereof.

The invention claimed is:

1. A fixation assembly comprising:
   a carriage block portion having at least one fixation hole configured to receive a bone fastener;
   a base portion that is elongate along a longitudinal direction, the base portion having a top surface, a bottom surface, and a recess that extends into the top surface so as to be defined by opposed sidewalls, the recess configured to receive the carriage block;
   a plate portion that is elongate along the longitudinal direction, the plate portion having a top surface, a bottom surface, and at least one bore that extends between said the top surface and the bottom surface, the plate portion configured to be aligned with the base portion along a transverse direction that is perpendicular to the longitudinal direction such that the bore is configured to receive a fastener to couple the plate portion to the base portion to thereby retain the carriage block portion within the recess and at a location between the base portion and the plate portion; and
   a shim portion that is configured to be received between the carriage block and one of the sidewalls;
   wherein the shim portion limits the translation of the carriage block portion within the recess relative to the base portion along the longitudinal direction.

2. The fixation assembly of claim 1 wherein the plate portion has one or more flanges along its lower surface that align the top surface of the base portion with the lower surface of the plate portion when the base portion and plate portion are coupled.

3. The fixation assembly of claim 1 wherein a resilient clip is disposed within the fixation hole to allow the bone fastener to angulate.

4. The fixation assembly of claim 1 wherein the carriage block portion comprises a pair of fixation holes and a connection portion between the pair of fixation holes.

5. The fixation assembly of claim 1 wherein the shim portion comprises nitinol.

6. The fixation assembly of claim 1 wherein the shim portion is made from a bioresorbable material.

7. The fixation assembly of claim 1 wherein the shim portion has flexible tabs that are configured to compress the shim portion to allow the shim portion to be received between the carriage block portion and the one of the sidewalls of the recess.

8. The fixation assembly of claim 1, wherein the base portion includes the opposed sidewalls.

9. The fixation assembly of claim 1, further comprising a second carriage block portion having at least one fixation hole configured to receive a second bone fastener, wherein the base portion further has a second recess that extends into the top surface so as to be defined by opposed second sidewalls, the second recess configured to receive the second carriage block.

10. The fixation assembly of claim 9, wherein the second recess is spaced apart from the recess along the longitudinal direction.

11. The fixation assembly of claim 10, wherein the carriage block is moveable along the longitudinal direction within the recess, and the second carriage block is moveable along the longitudinal direction within the second recess.

12. The fixation assembly of claim 10, further comprising a second shim portion that is configured to be received between the second carriage block and one of the second sidewalls of the second recess, wherein the second shim portion limits the translation of the second carriage block within the second recess relative to the base portion along the longitudinal direction.

13. A fixation assembly comprising:
    a first plate segment that is elongate along a longitudinal direction, the first plate segment having a first translating surface, at least one fixation hole, and a first recess;
    a carriage block that is elongate along the longitudinal direction, the carriage block having a second translating surface, at least one fixation hole, and a second recess that is at least partially aligned with the first recess along a transverse direction that is perpendicular to the longitudinal direction, and
    a shim that is configured to be receivable within at least a portion of the first recess and the second recess;
    wherein the first translating surface and the second translating surface interact to permit translation of the first plate segment and carriage block relative to each other along the longitudinal direction and the shim is configured to engage the carriage block to thereby limit said translation when the shim is received within at least a portion of the first recess and the second recess.

14. The fixation assembly of claim 13 wherein the shim is substantially polygonal shaped.

15. The fixation assembly of claim 14 wherein the first recess is substantially polygonal shaped.

16. The fixation assembly of claim 15 wherein the second recess is substantially polygonal shaped.

17. The fixation assembly of claim 13 wherein the shim further includes a spring that increases resistance when the first plate segment and carriage block are translated relative to each other along the longitudinal axis.

18. The fixation assembly of claim 13 wherein shim further includes a cantilevered portion that increases resistance when the first plate segment and carriage block are translated relative to each other along the longitudinal axis.

19. The fixation assembly of claim 13 wherein the shim comprises nitinol.

20. The fixation assembly of claim 13 wherein the shim is made from a bioresorbable material.

* * * * *